United States Patent
Martinez et al.

(10) Patent No.: US 10,010,336 B2
(45) Date of Patent: Jul. 3, 2018

(54) MEDICAL DEVICES WITH DETACHABLE PIVOTABLE JAWS

(71) Applicant: COOK MEDICAL TECHNOLOGIES LLC, Bloomington, IN (US)

(72) Inventors: Michelle D. Martinez, Winston-Salem, NC (US); Vihar C. Surti, Winston-Salem, NC (US); Tyler Evans McLawhorn, Winston-Salem, NC (US)

(73) Assignee: Cook Medical Technologies, Inc., Bloomington, IN (US)

( * ) Notice: Subject to any disclaimer, the term of this patent is extended or adjusted under 35 U.S.C. 154(b) by 31 days.

(21) Appl. No.: 14/484,824

(22) Filed: Sep. 12, 2014

(65) Prior Publication Data
US 2014/0379018 A1  Dec. 25, 2014

Related U.S. Application Data

(63) Continuation-in-part of application No. 13/270,851, filed on Oct. 11, 2011, now Pat. No. 9,339,270, which
(Continued)

(51) Int. Cl.
*A61B 17/28* (2006.01)
*A61B 17/29* (2006.01)
(Continued)

(52) U.S. Cl.
CPC .............. *A61B 17/29* (2013.01); *A61B 17/08* (2013.01); *A61B 17/10* (2013.01); *A61B 17/282* (2013.01);
(Continued)

(58) Field of Classification Search
CPC ...................... A61B 17/282; A61B 2017/2825
See application file for complete search history.

(56) References Cited

U.S. PATENT DOCUMENTS

| 720,385 A | 2/1903 | Storle |
| 2,384,697 A | 9/1945 | Riccardi |

(Continued)

FOREIGN PATENT DOCUMENTS

| DE | 4404766 A1 | 8/1995 |
| DE | 19534320 | 2/1997 |

(Continued)

OTHER PUBLICATIONS

International Search Report/Written Opinion for PCT/US2009/069270 (dated May 17, 2010).
(Continued)

*Primary Examiner* — Shaun L David
(74) *Attorney, Agent, or Firm* — Brinks Gilson & Lione

(57) ABSTRACT

Medical systems, devices and methods are provided for engaging tissue, e.g. for clipping tissue, closing a perforation or performing hemostasis. Generally, the medical system including a housing, first and second jaws rotatable relative to the housing, a driver, and an elongate drive wire. The elongate drive wire may be disconnected from the driver, first and second jaws, and the housing, which are left in vivo engaged with the tissue. The medical device of the system may include a biasing strip engaged with the jaws, and/or a gripping strip attached to at least one of the jaws to improve the engagement of the tissue between the jaws.

26 Claims, 25 Drawing Sheets

Related U.S. Application Data is a continuation-in-part of application No. 12/971,873, filed on Dec. 17, 2010, now Pat. No. 8,771,293.

(60) Provisional application No. 61/391,881, filed on Oct. 11, 2010, provisional application No. 61/289,297, filed on Dec. 22, 2009.

(51) Int. Cl.
*A61B 17/285* (2006.01)
*A61B 17/08* (2006.01)
*A61B 17/10* (2006.01)
*A61B 17/122* (2006.01)
*A61B 17/128* (2006.01)
*A61B 17/00* (2006.01)
*A61B 17/12* (2006.01)

(52) U.S. Cl.
CPC .......... *A61B 17/285* (2013.01); *A61B 17/122* (2013.01); *A61B 17/1285* (2013.01); *A61B 2017/00473* (2013.01); *A61B 2017/12004* (2013.01); *A61B 2017/2902* (2013.01); *A61B 2017/2931* (2013.01); *A61B 2017/2932* (2013.01); *A61B 2017/2936* (2013.01); *A61B 2017/2943* (2013.01); *A61B 2017/2944* (2013.01)

(56) References Cited

U.S. PATENT DOCUMENTS

| | | | |
|---|---|---|---|
| 2,598,901 | A | 6/1952 | Garland |
| 2,614,445 | A | 10/1952 | Riordan |
| 3,363,628 | A | 1/1968 | Wood |
| 3,378,010 | A * | 4/1968 | Codling ............... A61B 17/122 606/142 |
| 3,463,156 | A | 8/1969 | McDermott |
| 3,481,641 | A | 12/1969 | Berger et al. |
| 3,581,745 | A | 6/1971 | Eller |
| 3,867,944 | A | 2/1975 | Samuels |
| 3,924,303 | A | 12/1975 | Elliott |
| 3,932,918 | A | 1/1976 | Paskert |
| 3,958,576 | A | 5/1976 | Komiya |
| 4,453,756 | A | 6/1984 | Haag |
| 4,467,802 | A | 8/1984 | Maslanka |
| 4,512,345 | A | 4/1985 | Green |
| 4,519,392 | A | 5/1985 | Lingua |
| 4,569,131 | A | 2/1986 | Falk et al. |
| 4,733,664 | A | 3/1988 | Kirsch et al. |
| 4,763,668 | A | 8/1988 | Macek et al. |
| 4,765,335 | A | 8/1988 | Schmidt et al. |
| 4,805,618 | A | 2/1989 | Ueda et al. |
| 4,822,348 | A | 4/1989 | Casey |
| 4,950,273 | A | 8/1990 | Briggs |
| 4,955,897 | A | 9/1990 | Ship |
| 4,990,152 | A | 2/1991 | Yoon |
| 5,009,657 | A | 4/1991 | Cotey et al. |
| 5,029,355 | A | 7/1991 | Thai |
| 5,049,153 | A * | 9/1991 | Nakao ................... A61B 17/10 606/138 |
| 5,100,418 | A | 3/1992 | Yoon et al. |
| 5,100,430 | A | 3/1992 | Avellanet et al. |
| 5,133,727 | A | 7/1992 | Bales et al. |
| 5,141,519 | A | 8/1992 | Smith et al. |
| 5,147,357 | A | 9/1992 | Rose et al. |
| 5,152,778 | A | 10/1992 | Bales, Jr. et al. |
| 5,156,609 | A | 10/1992 | Nakao et al. |
| 5,174,276 | A | 12/1992 | Crockard |
| 5,192,298 | A | 3/1993 | Smith et al. |
| 5,201,743 | A | 4/1993 | Haber et al. |
| 5,209,747 | A | 5/1993 | Knoepfler |
| 5,211,655 | A | 5/1993 | Hasson |
| 5,222,961 | A | 6/1993 | Nakao et al. |
| 5,242,456 | A | 9/1993 | Nash et al. |
| 5,275,608 | A | 1/1994 | Forman et al. |
| 5,275,613 | A | 1/1994 | Haber et al. |
| 5,275,615 | A | 1/1994 | Rose |
| 5,282,806 | A | 2/1994 | Haber et al. |
| 5,304,183 | A | 4/1994 | Gourlay et al. |
| 5,306,283 | A | 4/1994 | Conners |
| 5,318,589 | A | 6/1994 | Lichtman |
| 5,368,606 | A | 11/1994 | Marlow et al. |
| 5,407,243 | A | 4/1995 | Riemann |
| 5,423,857 | A | 6/1995 | Rosenman et al. |
| 5,471,992 | A | 12/1995 | Banik et al. |
| 5,474,569 | A | 12/1995 | Zinreich et al. |
| 5,499,998 | A | 3/1996 | Meade |
| 5,501,693 | A | 3/1996 | Gravener |
| 5,507,758 | A * | 4/1996 | Thomason ......... A61B 17/0469 606/139 |
| 5,509,923 | A | 4/1996 | Middleman et al. |
| 5,520,701 | A | 5/1996 | Lerch |
| 5,542,432 | A * | 8/1996 | Slater ................. A61B 10/06 600/564 |
| 5,569,274 | A | 10/1996 | Rapacki et al. |
| 5,571,137 | A | 11/1996 | Marlow et al. |
| 5,584,855 | A | 12/1996 | Onik |
| 5,618,303 | A | 4/1997 | Marlow et al. |
| 5,620,452 | A | 4/1997 | Yoon |
| 5,626,607 | A | 5/1997 | Malecki et al. |
| 5,632,764 | A | 5/1997 | Beideman et al. |
| 5,634,932 | A | 6/1997 | Schmidt |
| 5,665,100 | A * | 9/1997 | Yoon ....................... A61F 6/206 606/139 |
| 5,702,407 | A | 12/1997 | Kaji |
| 5,728,121 | A * | 3/1998 | Bimbo ................... A61B 17/29 606/207 |
| 5,766,184 | A | 6/1998 | Matsuno et al. |
| 5,766,189 | A | 6/1998 | Matsuno |
| 5,782,747 | A | 7/1998 | Zimmon |
| 5,782,748 | A * | 7/1998 | Palmer .................. A61B 10/06 600/104 |
| 5,792,165 | A | 8/1998 | Kilieman et al. |
| 5,797,923 | A | 8/1998 | Aiyar et al. |
| 5,797,939 | A | 8/1998 | Yoon |
| 5,797,941 | A * | 8/1998 | Schulze ............. A61B 18/1442 606/171 |
| 5,797,958 | A * | 8/1998 | Yoon ....................... A61F 6/206 606/139 |
| 5,846,255 | A | 12/1998 | Casey |
| 5,893,863 | A | 4/1999 | Yoon |
| 5,893,875 | A | 4/1999 | O'Connor et al. |
| 5,893,878 | A | 4/1999 | Pierce |
| 5,902,310 | A | 5/1999 | Foerster et al. |
| 5,922,002 | A * | 7/1999 | Yoon ....................... A61F 6/206 606/139 |
| 5,964,779 | A | 10/1999 | Mayenberger et al. |
| 5,984,939 | A * | 11/1999 | Yoon ................ A61B 17/12013 606/139 |
| 6,007,552 | A * | 12/1999 | Fogarty ................ A61B 17/02 606/157 |
| 6,010,523 | A | 1/2000 | Sabin et al. |
| 6,059,719 | A | 5/2000 | Yamamoto et al. |
| 6,106,041 | A | 8/2000 | Eckhardt |
| 6,139,563 | A | 10/2000 | Cosgrove, III et al. |
| 6,258,105 | B1 * | 7/2001 | Hart .................... A61B 17/1285 606/142 |
| 6,358,197 | B1 | 3/2002 | Silverman et al. |
| 6,386,496 | B1 | 5/2002 | Lai et al. |
| 6,464,710 | B1 | 10/2002 | Foster |
| 6,613,059 | B2 | 9/2003 | Schaller et al. |
| 6,814,742 | B2 | 11/2004 | Kimura et al. |
| 6,923,818 | B2 | 8/2005 | Muramatsu et al. |
| 6,991,634 | B2 | 1/2006 | Sugiyama et al. |
| 7,011,667 | B2 | 3/2006 | Kobayashi et al. |
| 7,041,118 | B2 | 5/2006 | Muramatsu et al. |
| 7,081,121 | B2 | 7/2006 | Muramatsu et al. |
| 7,175,649 | B2 | 2/2007 | Nakao |
| 7,207,997 | B2 | 4/2007 | Shipp et al. |
| 7,223,271 | B2 | 5/2007 | Muramatsu et al. |
| 7,223,272 | B2 | 5/2007 | Francese et al. |
| 7,326,221 | B2 | 2/2008 | Sakamoto |

(56) References Cited

U.S. PATENT DOCUMENTS

| | | | |
|---|---|---|---|
| 7,452,327 B2 | 11/2008 | Durgin et al. | |
| 7,488,334 B2 | 2/2009 | Jugenheimer et al. | |
| 7,494,461 B2 | 2/2009 | Wells et al. | |
| 7,601,159 B2 | 10/2009 | Ewers et al. | |
| 7,722,628 B2 | 5/2010 | Stokes et al. | |
| 7,727,247 B2 | 6/2010 | Kimura et al. | |
| 7,736,372 B2 | 6/2010 | Reydel et al. | |
| 7,736,374 B2 | 6/2010 | Vaughan et al. | |
| 7,740,639 B2 | 6/2010 | Hummel et al. | |
| 7,744,613 B2 | 6/2010 | Ewers et al. | |
| 7,766,810 B2 | 8/2010 | Ohdaira | |
| 7,776,057 B2 | 8/2010 | Laufer et al. | |
| 7,815,652 B2 | 10/2010 | Messerly et al. | |
| 7,896,895 B2 | 3/2011 | Boudreaux et al. | |
| 8,062,311 B2 | 11/2011 | Litscher et al. | |
| 8,083,668 B2 | 12/2011 | Durgin et al. | |
| 8,088,061 B2 | 1/2012 | Wells et al. | |
| 8,172,859 B2 | 5/2012 | Matsuno et al. | |
| 8,317,820 B2 | 11/2012 | Surti | |
| 8,348,964 B2 | 1/2013 | Kimura et al. | |
| 8,545,519 B2 * | 10/2013 | Aguirre | A61B 17/08 606/142 |
| 8,709,027 B2 | 4/2014 | Adams et al. | |
| 8,771,293 B2 * | 7/2014 | Surti | A61B 17/08 606/142 |
| 8,858,588 B2 * | 10/2014 | Sigmon, Jr. | A61B 17/08 606/205 |
| 8,939,997 B2 * | 1/2015 | Martinez | A61B 17/08 606/1 |
| 8,979,891 B2 * | 3/2015 | McLawhorn | A61B 17/08 606/142 |
| 2001/0034536 A1 * | 10/2001 | Looper | A61B 17/122 606/205 |
| 2002/0045909 A1 | 4/2002 | Kimura et al. | |
| 2002/0151916 A1 | 10/2002 | Muramatsu et al. | |
| 2002/0173805 A1 | 11/2002 | Matsuno et al. | |
| 2003/0069592 A1 | 4/2003 | Adams et al. | |
| 2003/0097146 A1 | 5/2003 | Montalvo et al. | |
| 2003/0177861 A1 | 9/2003 | Terada | |
| 2004/0044363 A1 | 3/2004 | Fowler | |
| 2005/0033312 A1 * | 2/2005 | Suzuki | A61B 17/1285 606/110 |
| 2005/0059985 A1 | 3/2005 | Kimura | |
| 2005/0101991 A1 * | 5/2005 | Ahlberg | A61B 17/282 606/205 |
| 2005/0165429 A1 | 7/2005 | Douglas et al. | |
| 2005/0234296 A1 | 10/2005 | Saadat et al. | |
| 2005/0251183 A1 | 11/2005 | Buckman et al. | |
| 2005/0272977 A1 | 12/2005 | Saadat et al. | |
| 2006/0084886 A1 | 4/2006 | Reydel | |
| 2006/0155308 A1 * | 7/2006 | Griego | A61B 17/068 606/142 |
| 2006/0161182 A1 | 7/2006 | Vandenbroek | |
| 2006/0258905 A1 | 11/2006 | Kaji et al. | |
| 2006/0259045 A1 | 11/2006 | Damarati | |
| 2007/0073185 A1 | 3/2007 | Nakao | |
| 2007/0135678 A1 | 6/2007 | Suzuki | |
| 2007/0239162 A1 | 10/2007 | Bhatnagar et al. | |
| 2007/0250113 A1 | 10/2007 | Hegeman et al. | |
| 2007/0282355 A1 | 12/2007 | Brown et al. | |
| 2007/0287993 A1 | 12/2007 | Hinman et al. | |
| 2008/0004656 A1 | 1/2008 | Livneh | |
| 2008/0147113 A1 | 6/2008 | Nobis et al. | |
| 2008/0171907 A1 | 7/2008 | Long et al. | |
| 2008/0228199 A1 | 9/2008 | Cropper et al. | |
| 2008/0228202 A1 | 9/2008 | Cropper et al. | |
| 2008/0234703 A1 | 9/2008 | Cropper et al. | |
| 2008/0234705 A1 | 9/2008 | Cropper et al. | |
| 2008/0255427 A1 * | 10/2008 | Satake | A61B 17/08 600/204 |
| 2008/0262539 A1 | 10/2008 | Ewers et al. | |
| 2008/0269557 A1 | 10/2008 | Marescaux et al. | |
| 2008/0269566 A1 | 10/2008 | Measamer | |
| 2008/0275441 A1 | 11/2008 | Aue | |
| 2008/0287963 A1 | 11/2008 | Rogers et al. | |
| 2008/0294178 A1 | 11/2008 | Kortenbach et al. | |
| 2008/0300461 A1 | 12/2008 | Shaw et al. | |
| 2008/0300624 A1 | 12/2008 | Schwemberger et al. | |
| 2009/0005638 A1 | 1/2009 | Zwolinski | |
| 2009/0018602 A1 | 1/2009 | Mitelberg et al. | |
| 2009/0043316 A1 | 2/2009 | Durgin et al. | |
| 2009/0062792 A1 | 3/2009 | Vakharia et al. | |
| 2009/0138006 A1 | 5/2009 | Bales et al. | |
| 2009/0138028 A1 | 5/2009 | Wells et al. | |
| 2009/0143794 A1 | 6/2009 | Conlon et al. | |
| 2009/0163934 A1 | 6/2009 | Raschdorf, Jr. et al. | |
| 2009/0171380 A1 | 7/2009 | Whiting | |
| 2009/0192344 A1 | 7/2009 | Bakos et al. | |
| 2009/0221915 A1 | 9/2009 | Voegele et al. | |
| 2009/0299385 A1 | 12/2009 | Stefanchik et al. | |
| 2009/0306683 A1 | 12/2009 | Zwolinski et al. | |
| 2009/0306686 A1 | 12/2009 | Ohdaira | |
| 2009/0326518 A1 | 12/2009 | Rabin | |
| 2009/0326578 A1 | 12/2009 | Ewers et al. | |
| 2010/0010512 A1 | 1/2010 | Taylor et al. | |
| 2010/0042115 A1 | 2/2010 | Saadar et al. | |
| 2010/0057078 A1 | 3/2010 | Arts et al. | |
| 2010/0057085 A1 | 3/2010 | Holcomb et al. | |
| 2010/0130817 A1 | 5/2010 | Conlon | |
| 2010/0168787 A1 | 7/2010 | Surti | |
| 2010/0179540 A1 | 7/2010 | Marczyk et al. | |
| 2010/0198149 A1 | 8/2010 | Fox | |
| 2010/0198248 A1 | 8/2010 | Vakharia | |
| 2010/0211086 A1 | 8/2010 | Ewers et al. | |
| 2010/0217151 A1 | 8/2010 | Gostout et al. | |
| 2010/0217292 A1 | 8/2010 | Kimura et al. | |
| 2010/0217293 A1 | 8/2010 | Kimura et al. | |
| 2010/0217294 A1 | 8/2010 | Kumura et al. | |
| 2010/0249498 A1 | 9/2010 | Wingardner et al. | |
| 2010/0249700 A1 | 9/2010 | Spivey | |
| 2010/0249808 A1 | 9/2010 | Harada et al. | |
| 2011/0152888 A1 | 6/2011 | Ho et al. | |
| 2012/0016391 A1 * | 1/2012 | Aguirre | A61B 17/08 606/151 |
| 2012/0089158 A1 | 4/2012 | Martinez et al. | |
| 2012/0089176 A1 | 4/2012 | Sigmon, Jr. et al. | |
| 2012/0109160 A1 | 5/2012 | Martenez et al. | |
| 2012/0165863 A1 | 6/2012 | McLawhorn | |
| 2012/0232338 A1 | 9/2012 | Livneh | |
| 2012/0051200 A1 | 11/2012 | Martenez et al. | |
| 2013/0046334 A1 | 2/2013 | Jones et al. | |

FOREIGN PATENT DOCUMENTS

| | | |
|---|---|---|
| DE | 19750878 A1 | 5/1999 |
| DE | 19906360 A1 | 8/2000 |
| DE | 102006003548 | 8/2007 |
| EP | 0246087 A3 | 11/1987 |
| EP | 0 380 874 A1 | 8/1990 |
| EP | 0541930 A1 | 5/1993 |
| EP | 0738501 A1 | 10/1996 |
| FR | 790997 | 11/1935 |
| GB | 2476461 A | 6/2011 |
| JP | 57-156752 | 9/1982 |
| JP | 60-103946 | 6/1985 |
| JP | 63-6016 | 2/1988 |
| JP | 63-267345 | 11/1988 |
| JP | 63-288147 | 11/1988 |
| JP | 2-6011 | 1/1990 |
| JP | 2007950 | 1/1990 |
| JP | 4-26091 | 3/1992 |
| JP | 4102450 | 4/1992 |
| JP | 5-212043 | 8/1993 |
| JP | 5208020 | 8/1993 |
| JP | 5212042 | 8/1993 |
| JP | 6237939 | 8/1994 |
| JP | 6254101 | 9/1994 |
| JP | 8019548 | 1/1996 |
| JP | 8126648 | 5/1996 |
| JP | 8280701 | 10/1996 |
| JP | 8308847 | 11/1996 |
| JP | 1997-508540 | 2/1997 |
| JP | 9038093 | 2/1997 |

(56) References Cited

FOREIGN PATENT DOCUMENTS

| JP | 9289989 | 11/1997 |
|---|---|---|
| JP | 2000-33090 | 2/2000 |
| JP | 2000-335631 | 12/2000 |
| JP | 2001-520069 | 10/2001 |
| JP | 2002-224124 | 8/2002 |
| JP | 2002-301082 | 10/2002 |
| JP | 2002-360585 | 12/2002 |
| JP | 2005-525904 A | 9/2005 |
| JP | 2006-528911 A | 12/2006 |
| JP | 2006-528911 A5 | 7/2007 |
| JP | 2006-528911 A5 | 5/2010 |
| JP | 2013-544128 A | 12/2013 |
| WO | WO 95/20914 | 8/1995 |
| WO | WO 9614020 | 5/1996 |
| WO | WO 99/20183 | 4/1999 |
| WO | WO 03/099139 A1 | 12/2003 |
| WO | WO 2004 023976 A2 | 3/2004 |
| WO | WO 2004/017839 | 4/2004 |
| WO | WO 2004/103162 A2 | 12/2004 |
| WO | WO 2008/005433 | 1/2008 |
| WO | WO 2010/078163 | 7/2010 |
| WO | WO 2011/087723 | 7/2011 |
| WO | WO 2012/051188 | 4/2012 |
| WO | WO 2012/051191 | 4/2012 |
| WO | WO 2012/051200 | 4/2012 |
| WO | WO 2012/083041 | 6/2012 |

OTHER PUBLICATIONS

International Search Report/Written Opinion for PCT/US2010/061077 (dated Apr. 1, 2011).
Olympus Endo Therapy brochure on the QuickClip2 Long.
CooperSurgical brochure on the Marlow Nu-Tip Laparoscopic Instruments.
Medwork brochure,Endo Therapy for the Clipmaster 3.
Boston Scientific Catalog on the Resolution Clip Device.
Medicon Instrument Catalog, pp. 440, 441, 443, 451, 585, 686 (1986).
V. Mueller, The Surgical Armamentarium, pp. F176-F177 (1988).
Annex to Form PCT/ISA/206—Communication Relating to the Results of Partial International Search for PCT/US2011/055800 (dated Jun. 28, 2012).
International Search Report and Opinion for PCT/US2011/055780 (dated Jun. 14, 2012).
International Search Report and Opinion for PCT/US2011/055786 (dated Jun. 19, 2012).
International Search Report and Opinion for PCT/US2011/065200 (dated Jun. 13, 2012).
Office Action dated Dec. 24, 2013 U.S. Appl. No. 13/270,784 in related application.
International Search Report and Opinion for PCT/US2011/055800 (dated Sep. 12, 2012).
International Search Report and Opinion for PCT/US2012/046666 (dated Oct. 8, 2012).
Office Action dated Jan. 18, 2012 for U.S. Appl. No. 12/645,004 in related application.
Office Action dated May 29, 2012 for U.S. Appl. No. 12/645,004 in related application.
Office Action dated Dec. 20, 2012 for U.S. Appl. No. 13/186,427 in related application.
Office Action dated May 6, 2013 for U.S. Appl. No. 12/971,873 in related application.
Office Action dated Nov. 6, 2013 for U.S. Appl. No. 12/971,873 in related application.
Office Action dated Mar. 10, 2014 for U.S. Appl. No. 13/270,851 in related application.
Office Action dated Mar. 17, 2014 for U.S. Appl. No. 13/270,834 in related application.
Office Action dated Feb. 26, 2014 for U.S. Appl. No. 13/327,127 in related application.
Product brochure entitled "Hemostatic Grasper" , 2014 Olympus America, Inc., Jul. 1, 2014, pp. 1-3 (https://medical.olympusamerica.com/products/coagrasper).
Product brochure entitled "Titanium Hemostatic Clip", Jorgensen Laboratories, Inc., Loveland, Colorado 80538.
Partial European Search Report, Application No. 17159385.8, dated Jun. 17, 2017, 8 pages.
Extended European Search Report, Application No. 17 198 794.4, dated Feb. 2, 2018, 8 pages.

* cited by examiner

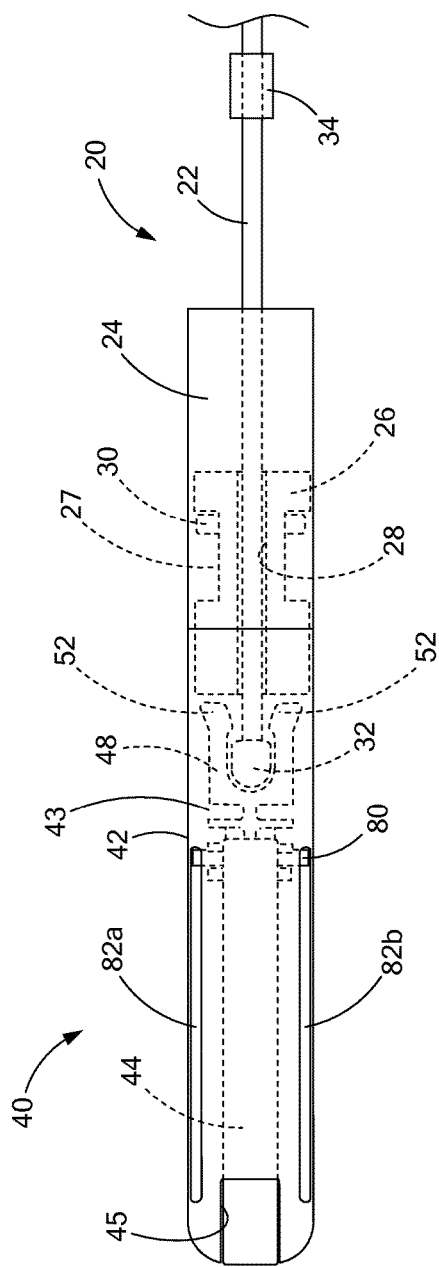
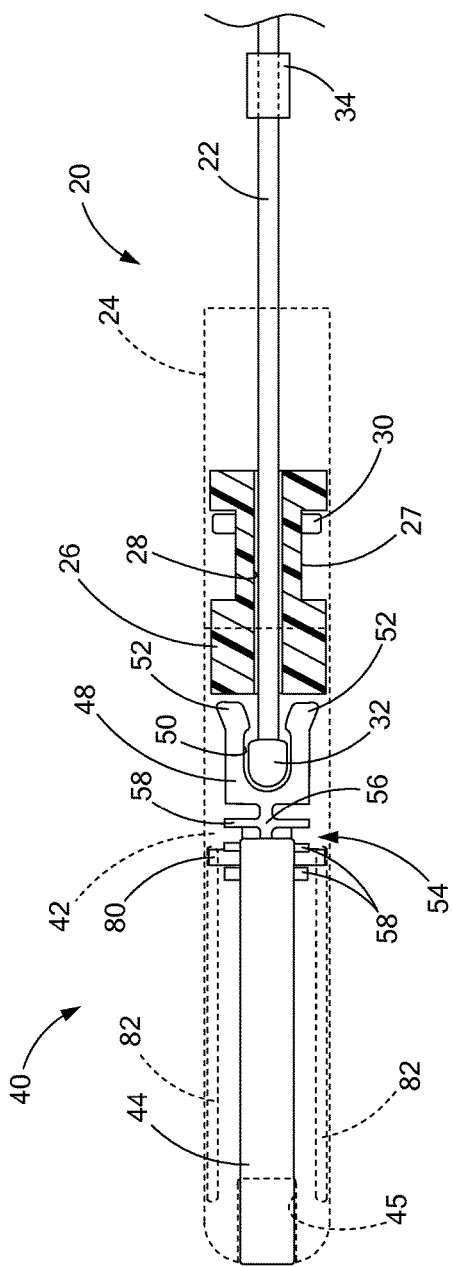
FIG. 1
FIG. 2

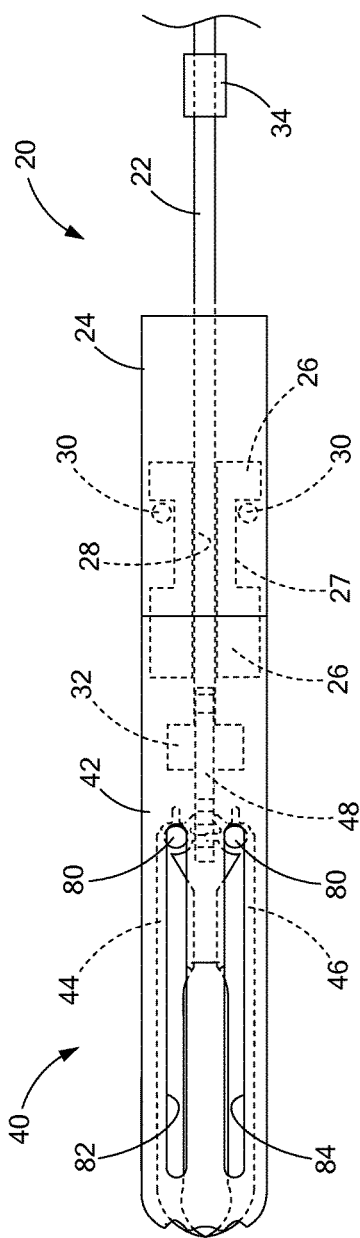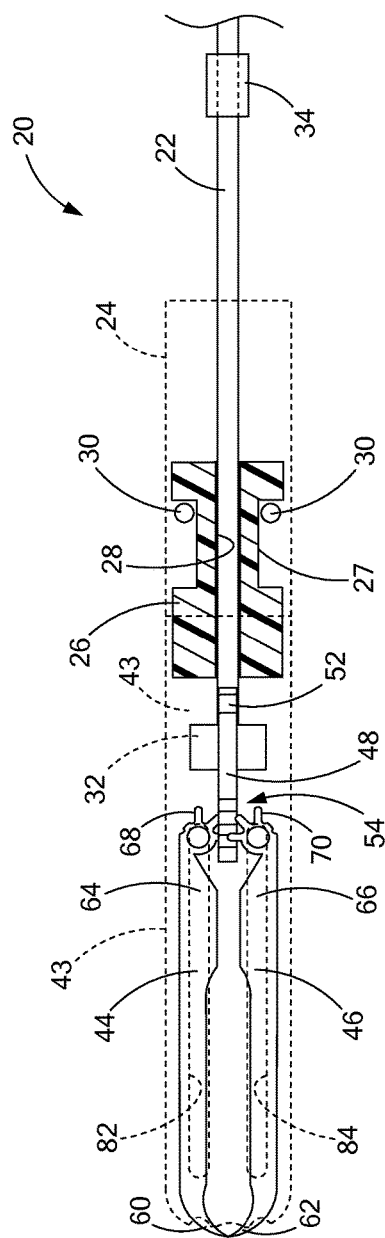

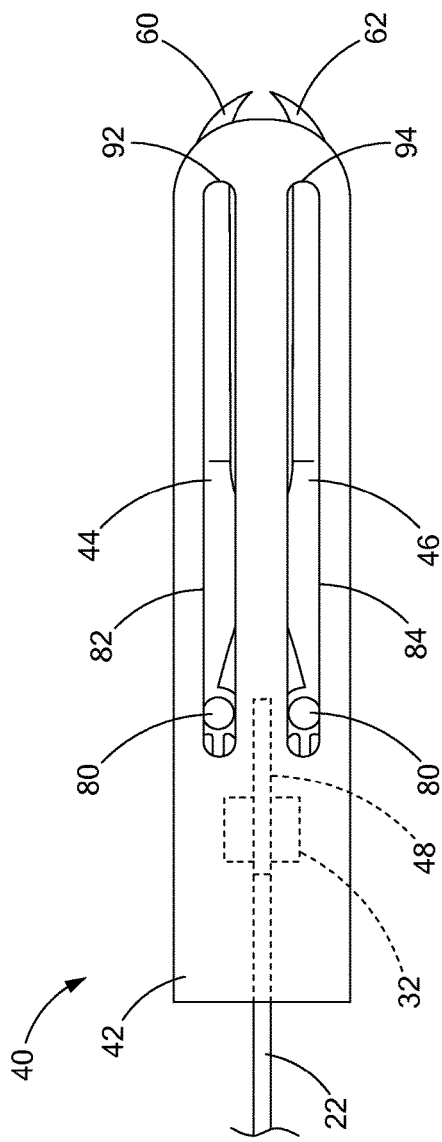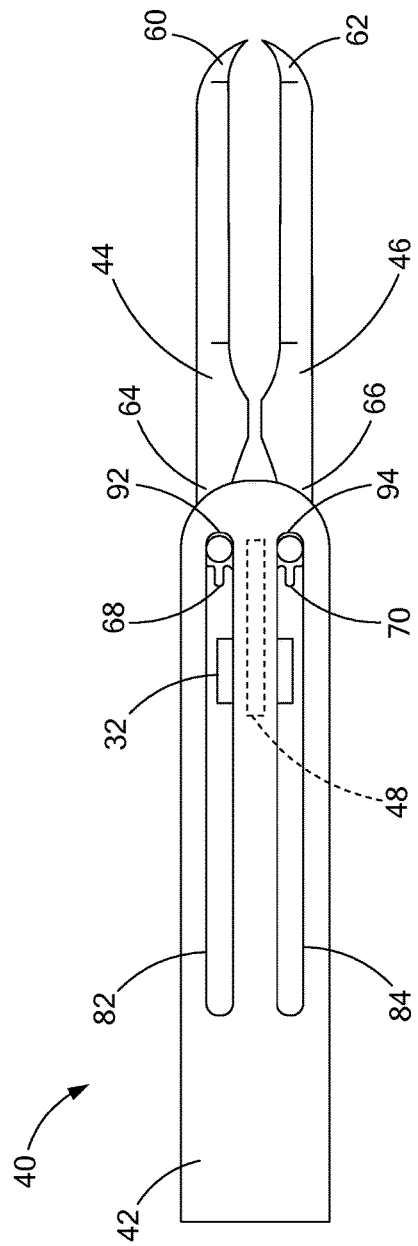
FIG. 8
FIG. 9

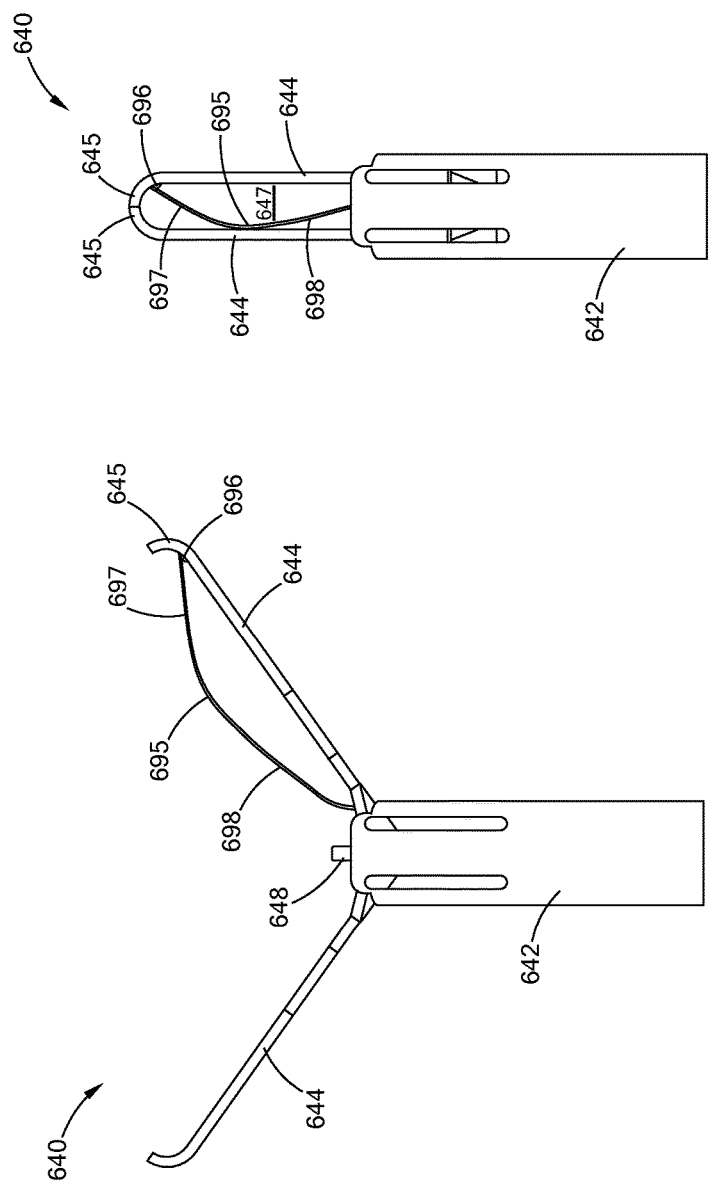

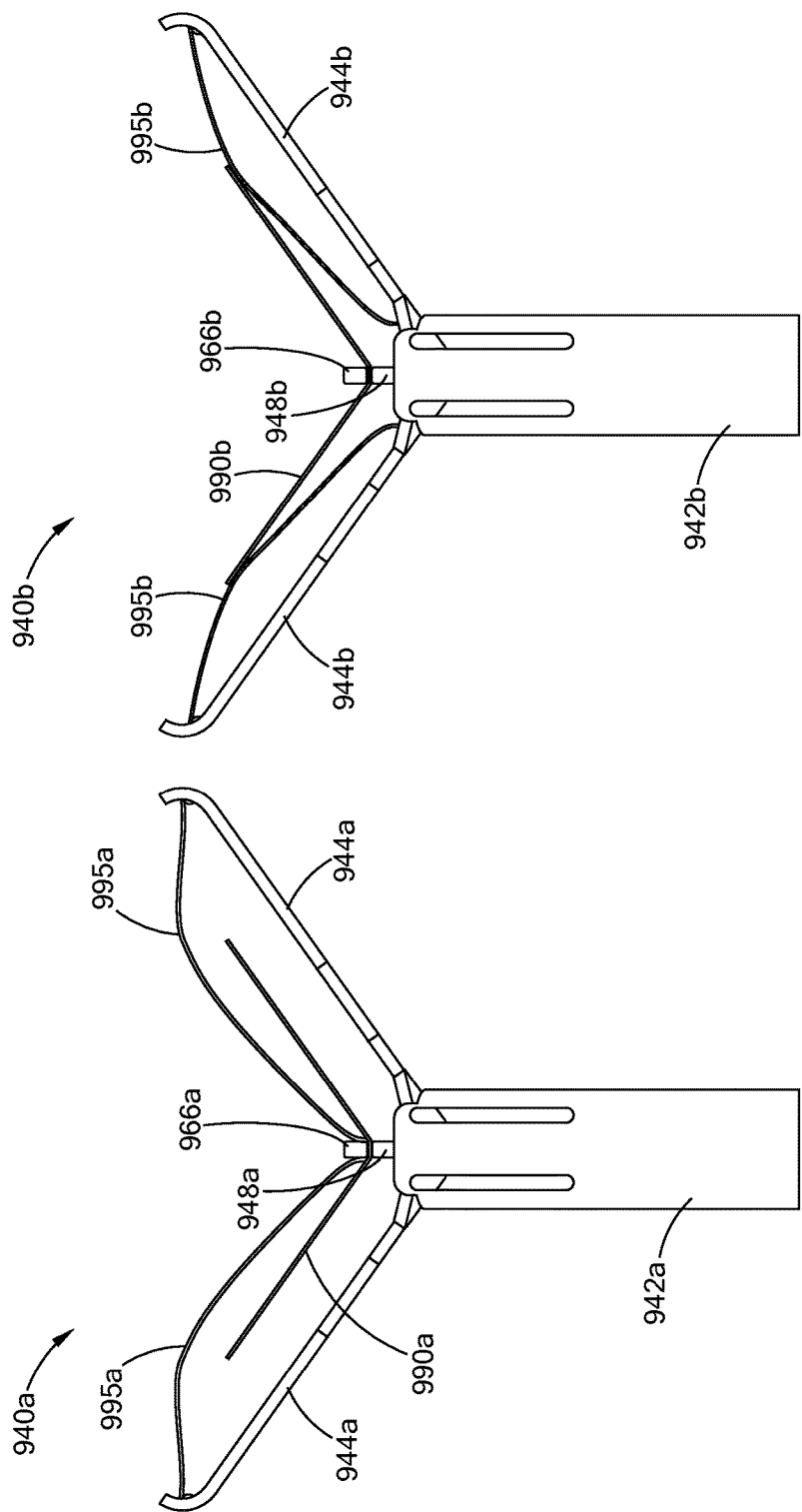

MEDICAL DEVICES WITH DETACHABLE PIVOTABLE JAWS

CROSS-REFERENCE TO RELATED APPLICATIONS

This application is a Continuation-In-Part of U.S. patent application Ser. No. 13/270,851 filed Oct. 11, 2011, which claims the benefit of U.S. Provisional Patent Application Ser. No. 61/391,881 filed on Oct. 11, 2010, and is also a Continuation-In-Part of U.S. patent application Ser. No. 12/971,873 filed on Dec. 17, 2010, now U.S. Pat. No. 8,771,293, which claims the benefit of U.S. Provisional Patent Application Ser. No. 61/289,297 filed on Dec. 22, 2009. All of the foregoing applications are hereby incorporated by reference.

BACKGROUND

Conventionally, a clip may be introduced into a body cavity through an endoscope to grasp living tissue of a body cavity for hemostasis, marking, and/or ligating. Such clips are often known as surgical clips, endoscopic clips, hemostasis clips and vascular clips. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding. Clips have also been attempted for use in closing perforations in the stomach Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high morbidity rate and many other undesirable side effects, there exists a need for highly effective, less invasive procedures.

Mechanical hemostatic devices such as clips have been used in various parts of the body, including gastrointestinal applications. One of the problems associated with conventional hemostatic devices and clips, however, is that many devices are not strong enough to cause permanent hemostasis. Further, clips have also been attempted for use in closing perforations in the stomach or gastrointestinal structures, but unfortunately traditional clips suffer from difficult placement and the capability to grasp a limited amount of tissue, potentially resulting in incomplete closure.

SUMMARY

The invention may include any of the following aspects in various combinations and may also include any other aspect described below in the written description or in the attached drawings.

In a first aspect, a medical device is provided for engaging tissue, the medical device including a housing, first and second jaws, a driver, a biasing strip, and a drive wire. The housing defines an internal passageway and a longitudinal axis extending between proximal and distal ends of the housing. The first and second jaws are rotatable relative to the housing, and have proximal and distal ends. The driver is engaged with the proximal ends of the first and second jaws, whereby longitudinal movement of the driver rotates the first and second jaws relative to the housing. The biasing strip is operatively connected to at least one of the first and second jaws to bias the jaws radially. The biasing strip includes at least one projection extending radially inwardly towards the longitudinal axis, the at least one projection sized and structured to engage the tissue between the first and second jaws. The elongated drive wire is selectively connected to the driver for longitudinal movement therewith.

According to more detailed aspects, the biasing strip biases the first and second jaws radially outwardly, and preferably is directly attached to the driver and directly engages each of the first and second jaws. The at least one projection preferably has a triangular shape terminating in a sharp distal end for piercing tissue, and is formed by stamping the biasing strip. The biasing strip may include a first portion adjacent the first jaw, and a second portion adjacent the second jaw, wherein the at least one projection includes a first projection on the first portion of the biasing strip and a second projection on the second portion of the biasing strip. The biasing strip can be directly attached to the driver at a location between the first and second portions. The first and second jaws are preferably non-detachably connected to the housing. A first end of the biasing strip may engage the first jaw while a second end of the biasing strip may engage the second jaw. A middle portion of the biasing strip is preferably fixed to a distal end of the driver and moves therewith.

In a second aspect a medical device is provided for engaging tissue, the medical device including a housing, first and second jaws, a driver, and a gripping strip. The housing defines an internal passageway and a longitudinal axis extending between proximal and distal ends of the housing. The first and second jaws are rotatable relative to the housing, and have proximal and distal ends. The driver is engaged with the proximal ends of the first and second jaws, whereby longitudinal movement of the driver rotates the first and second jaws relative to the housing. The gripping strip is positioned between the first and second jaws and attached to a distal portion of the first jaw. The gripping strip projects towards the second jaw and is positioned to engage tissue between the second jaw and the gripping strip.

According to more detailed aspects, in a closed position of the medical device, the first and second jaws each include distal ends that engage each other, and also include portions proximal to their distal ends that are spaced apart to define a gripping space therebetween. Preferably, the gripping strip projects through the gripping space to a location immediately adjacent the second jaw. The gripping strip may engage the second jaw in the closed position when no tissue is located between the first and second jaws. The gripping strip preferably includes a distal portion extending laterally towards the second jaw, and a proximal portion extending radially away from the second jaw. A proximal end of the gripping strip may be free floating. The gripping strip may also include at least one projection extending radially inwardly towards the longitudinal axis, the at least one projection sized and structured to engage the tissue between the first and second jaws According to further detailed aspects, the medical device may further include a biasing strip positioned between the first and second jaws, the biasing strip operatively connected to at least one of the first and second jaws to bias the jaws radially. The proximal end of the gripping strip may be positioned between the biasing strip and the first jaw, or may be positioned between the biasing strip and the second jaw. A second gripping strip may also positioned between the first and second jaws, the second gripping strip attached to a distal portion of the second jaw, the second gripping strip projecting towards the first jaw and positioned to engage tissue between the first and second gripping strips.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a top view of a medical system having a medical device for engaging tissue, constructed in accordance with the teachings of the present invention;

FIG. 2 is a top view similar to FIG. 1, but showing the outer structures in dotted lines and the interior sections in solid lines and partial cross section;

FIG. 3 is a side view of the medical system and device depicted in FIG. 1;

FIG. 4 is a side view similar to FIG. 3, but showing the outer structures in dotted lines and the interior structures in solid lines and partial cross section

FIGS. 8-12 are side views showing operation of the medical system and device depicted in FIGS. 1-5;

FIG. 22b is a plan view of the driver of FIG. 19 shown attached to a strip and forming a portion of the medical device of FIG. 22a;

FIGS. 37 to 39 are side views showing operation of another alternate embodiment of the medical device depicted in FIG. 1;

FIG. 43 is a side view of another alternate embodiment of the medical device depicted in FIG. 1; and FIG. 44 is a side view of another alternate embodiment of the medical device depicted in FIG.

DETAILED DESCRIPTION

Figure 5:
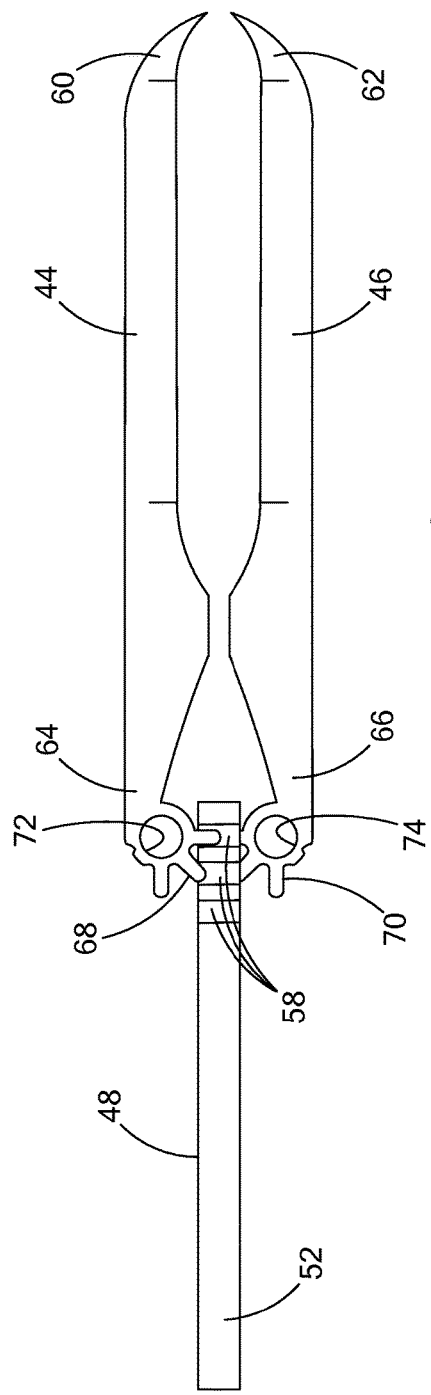
FIG. 5 is a side view of a medical device that is part of the medical system depicted in FIGS. 1-4.

The terms "proximal" and "distal" as used herein are intended to have a reference point relative to the user. Specifically, throughout the specification, the terms "distal" and "distally" shall denote a position, direction, or orientation that is generally away from the user, and the terms "proximal" and "proximally" shall denote a position, direction, or orientation that is generally towards the user.

An exemplary medical system 20 having a medical device 40 for engaging tissue T (FIG. 11) is shown in FIGS. 1 through 4. The medical system 20 and device 40 are generally sized and structured for operation through the working channel of an endoscope (not shown) or other scope, although the system 20 and device 40 may also be used alone or in conjunction with other elongate devices such as catheters, fiber-optic visualization systems, needles and the like. Generally, the medical system 20 includes a drive wire 22 slidably housed within the distal end 23 of an elongated catheter 24 for selective connection to, and operation of, the medical device 40. As will be described in further detail herein, the medical device 40 generally includes a housing 42 having a first jaw 44 and a second jaw 46 pivotally connected thereto for engaging the tissue T. Generally, the jaws 44, 46 have been shown as forming grasping forceps, although the jaws are intended to be used to clip tissue, e.g. to close an opening or for hemostasis. Accordingly, it will be recognized that the shape and structure of the jaws may take many forms and serve many purposes and functions, all in accordance with the teachings of the present invention.

In the medical system 20, the drive wire 22 slidably extends through the catheter 24. Although the term "wire" is used to refer to the drive wire 22, it will be recognized that any elongate control member capable of transmitting longitudinal force over a distance (such as is required in typical endoscopic, laparoscopic and similar procedures) may be used, and this includes plastic rods or tubes, single filament or multi-filament wires, metal rods and the like. The drive wire 22 should also be capable of properly transmitting a rotational/torsional force from the proximal end to the distal end to rotate the medical device 40 and jaws 44, 46, and thus it is currently preferred that the drive wire 22 is formed from nitinol (e.g. a nitinol wire) or other superelastic alloy. A connection block 26 is slidably fitted within the distal end 23 of the catheter 24 and defines a bore 28 therethrough which slidably receives the drive wire 22. The exterior of the connection block 26 includes a recessed portion 27, and two pins 30 (e.g., formed from stainless steel wire) are connected to the catheter 24 and positioned within the recessed portion 27 to limit the longitudinal movement of the connection block 26.

A distal end of the drive wire 22 defines a distal head 32 that is sized larger than the drive wire 22, and likewise larger than the bore 28 in the connection block 26. As will be described later herein, the distal head 32 is used to slide the connection block 26 within the catheter 24 to disconnect the medical device 40 from the medical system 20. As also seen in FIGS. 1-4, the housing 42 of the medical device 40 is a tubular member defining an interior space 43. A proximal end of the housing 42 frictionally receives a distal end of the connection block 26 within the interior space 43 for selective connection therewith.

The internal passageway 43 of the housing 42 also receives the first and second jaws 44, 46 and a driver 48 which is used to interconnect the drive wire 22 to the jaws 44, 46. As best seen in FIGS. 1, 2 and 5, the driver 48 has a proximal portion which defines a socket 50 sized to receive enlarged distal head 32 of the drive wire 22. At the proximal entrance of the socket 50, two deflectable locking tabs 52 are formed which rotate relative to the remainder of the driver 48 to increase or decrease the size of the socket 50. The locking tabs 52 may be separately formed and pivotally attached to the driver 48, or may be integrally formed with the driver 48 and formed of a resilient material which flexes to permit rotation of the locking tabs 52 radially inwardly and radially outwardly. A distal portion of the driver 48 defines a rack 54 for engaging and operating the jaws 44, 46. In the depicted embodiment, the rack 54 includes a central spine 56 having teeth 58 projecting away from the central spine 56 and on opposite sides of the spine 56. One set of teeth 58 on one side of the spine 56 generally operate the first jaw 44 while the other set of teeth 58 on the other side of the spine 56 operate the second jaw 46. It will be recognized that the rack 54 may include a single set of teeth or other geared structures that interface with the jaws 44, 46.

As best seen in FIG. 5, the first and second jaws 44, 46 include distal ends 60, 62 that are structured to grasp and engage tissue, generally they have a talon shape as disclosed in 61/141,934 filed Dec. 31, 2008, the disclosure of which is incorporated herein by reference in its entirety. The proximal ends 64, 66 of the first and second jaws 44, 46 each include a pinion gear 68, 70 having a series of teeth. The teeth of the pinion 68, 70 mesh with the teeth of the rack 54 of the driver 48 such that longitudinal translation of the driver 48 induces rotation in the first and second jaws 44, 46 relative to one another. Generally, distal translation of the driver 48 causes the first and second jaws 44, 46 to rotate outwardly away from each other, while proximal retraction of the driver 48 causes the first and second jaws 44, 46 to rotate inwardly toward one another. Pins 80 are fitted through each the proximal ends of the jaws 44, 46, to pivotally connect the jaws to the housing 42. Other structures for forming a pivotal connection may be used, and preferably the pivotal connection is centrally arranged relative to the pinions 68, 70.

Figure 7:
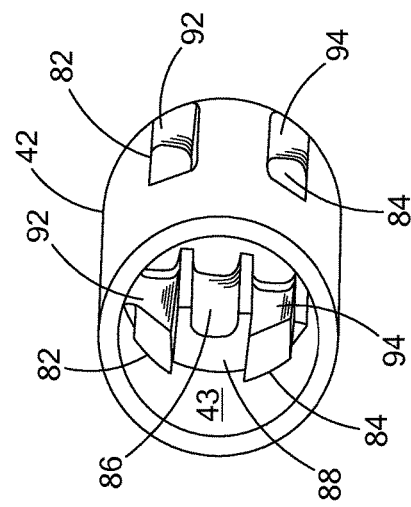
FIG. 7 is a perspective view of the housing depicted in FIG. 6.
Figure 6:
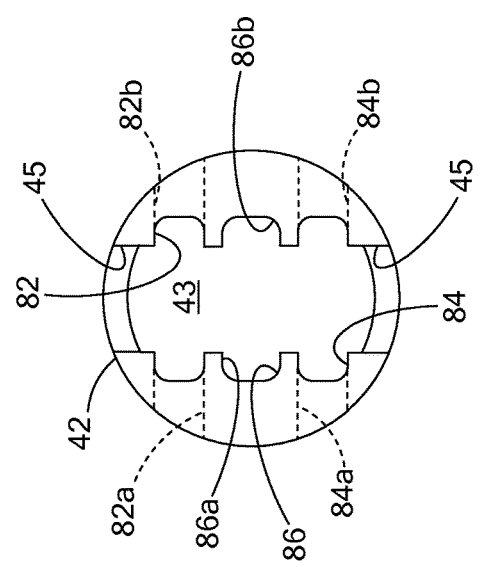
FIG. 6 is a front view of a housing forming a portion of the medical system and device depicted in FIGS. 1-5.

In addition to the jaws 44, 46 being pivotally attached to the housing 42, the first and second jaws 44, 46 are also slidably attached to the housing 42. As best seen in FIGS. 6 and 7 (and in conjunction with FIGS. 1-4) the housing 42 defines a first guide surface 82 for the first jaw 44, and a second guide surface 84 for the second jaw 46. As seen in FIG. 3, the first and second guide surfaces 82, 84 are formed by elongated slots 82a, 82b, 84a, 84b formed in opposing sides of the housing 42 which leaves a thickness of the housing 42 exposed to serve as the guide surface. The slots 82a, 82b are aligned to receive the connecting pin 80 of the first jaw 44, and likewise the slots 84a, 84b are aligned to receive the connecting pin 80 of the second jaw 46. The ends of the slots, for example distal ends 92, 94 shown in FIG. 7, serve to restrict the longitudinal movement of the jaws 44, 46 relative to the housing 42. The proximal ends 64, 66 of the jaws 44, 46 include apertures 72, 74 which receive the pins 80 (FIGS. 1, 2 and 3) that are used to slidably and pivotally connect the first and second jaws 44, 46 to the housing 42.

It can also be seen in FIGS. 6 and 7 that the housing 42 defines a third guide surface 86 which guides the longitudinal movement of the driver 48 within the housing 42. The guide surface 86 in the depicted embodiment includes a left guide surface 86a and a right guide surface 86b formed as C-shaped channels. As shown in FIG. 7, the third guide surface 86 transitions from a smaller proximal width to a larger distal width to define a shoulder 88 at the transition, which will be further described hereinbelow with reference to FIGS. 13 and 14.

As also shown in FIG. 6, the internal passageway 43 of the housing 42 extends through the distal end of the housing, and through which the first and second jaws 44, 46 can extend. Additionally, as shown in FIGS. 1 and 2, the housing 42 defines opposing slots 45 which are sized to permit the first and second jaws 44, 46 to pass therethrough when they rotate radially outwardly. Accordingly, it is also clear from FIGS. 1 and 2 that the housing 42 serves to block rotation of the first and second jaws 44, 46 when they are entirely or partially contained within the internal passageway 43 of the housing 42. Suitable plastics for forming the housing include, but are not limited to, polytetrafluorethylene (PTFE), expanded polytetrafluorethylene (EPTFE), polyethylene ether keytone (PEEK), polyvinylchloride (PVC), polycarbonate (PC), polyamide, polyimide, polyurethane, polyethylene (high, medium or low density), and suitable metals include stainless steel, nitinol and similar medical grade metals and alloys.

Operation of the medical device 40 will now be described with reference to FIGS. 8-12. As shown in FIG. 8, the first and second jaws 44, 46 are shown in a retracted position where they are substantially contained within the housing 42. Depending on the application, the distal ends 60, 62 of the jaws 44, 46 may slightly project from the distal end of the housing 42 in their retracted positions, or they may be entirely positioned within the housing 42. When the drive wire 22 is translated distally (to the right on the page in FIG. 8) the distal head 32 engages the driver 48, the driver 48 and jaws 44, 46 slide distally through the housing 42. The driver 48 and jaws 44, 46 slide longitudinally before they rotate (even though the rack 54 of the driver 48 is meshed with the pinions 68, 70 at the proximal ends 64, 60 of the jaws 44, 46) since the resistance to longitudinal movement is less than the force required to rotate the jaws 44, 46 (alternatively, the housing 42 can block rotation of the jaws 44, 46 when they are within the housing 42). As previously mentioned, this longitudinal movement is guided by the first and second guide surfaces 82, 84 which receive the pins 80 that slidably and pivotally connect the jaws 44, 46 to the housing 42.

Figure 10:
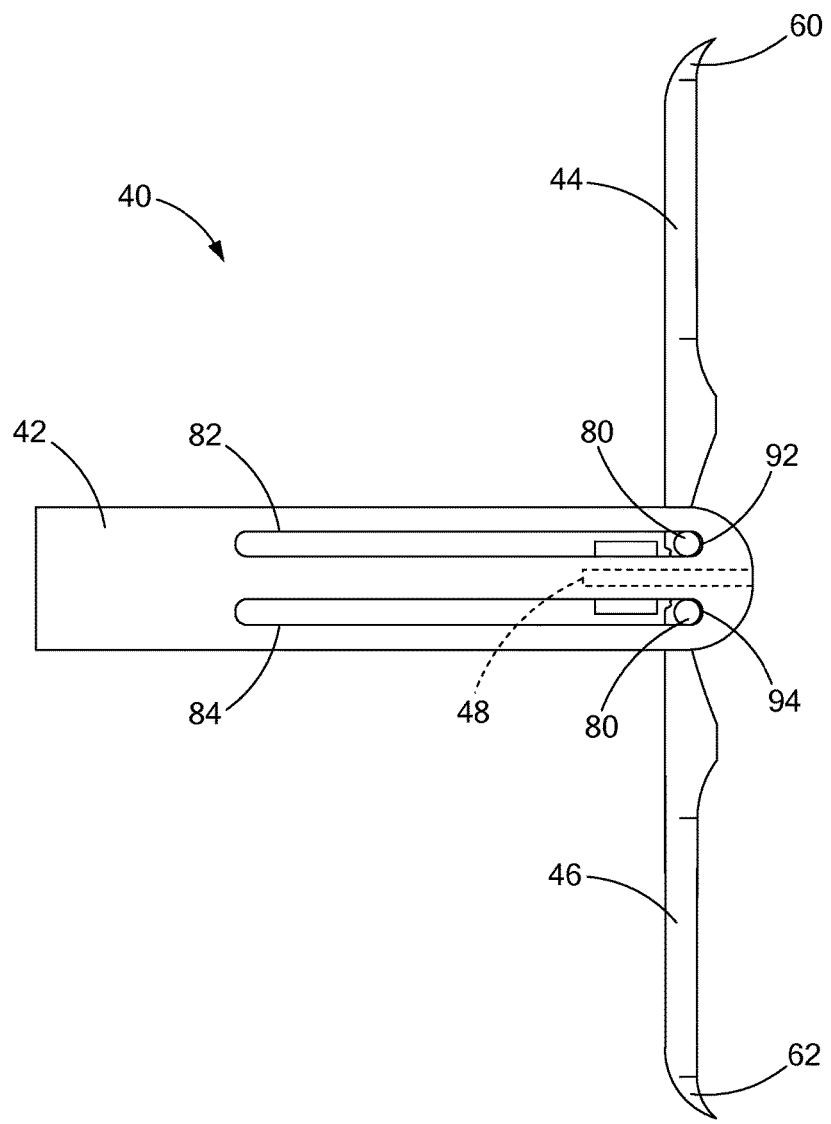

As shown in FIG. 9, the first and second jaws 44, 46 have an extended position where the jaws substantially project from a distal end of the housing 42, and their proximal ends 64, 66 are positioned adjacent the distal end of the housing 42. Accordingly, it will be seen that further distal advancement of drive wire 22, and hence the driver 48, causes the pinion 68 to rotate over the teeth 58 of the rack 54. As best seen in FIG. 10, the first and second jaws 44, 46 rotate radially outwardly from each other into a tissue receiving position. Notably, due to the presence of slots 45 at the distal end of the housing 42, the jaws 44, 46 are permitted to rotate a full 90°, thus forming at least a 180° between them. It will be recognized that through the sizing of the slots 45 and the construction of the rack 54 and pinions 68, 70, the first and second jaws 44, 46 may rotate even further away from each other.

Figure 11:
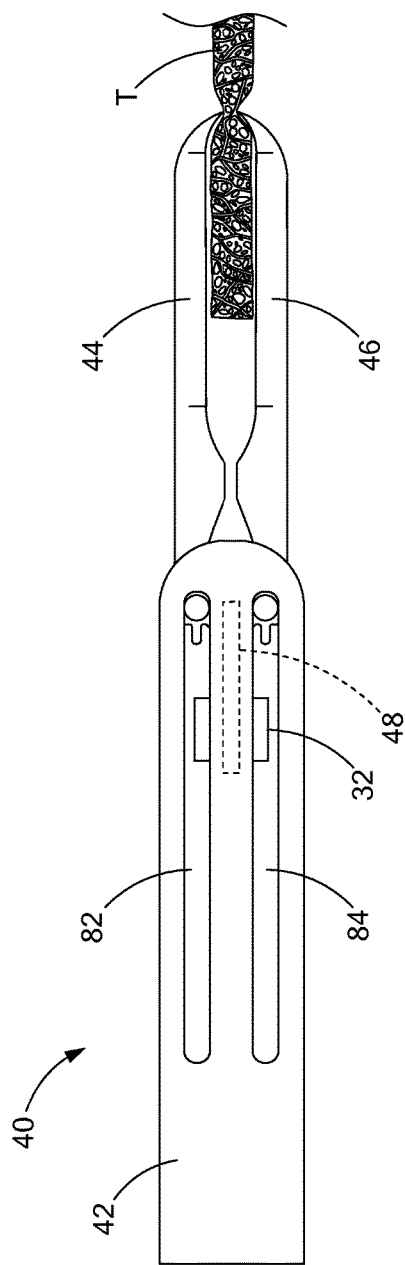
Figure 12:
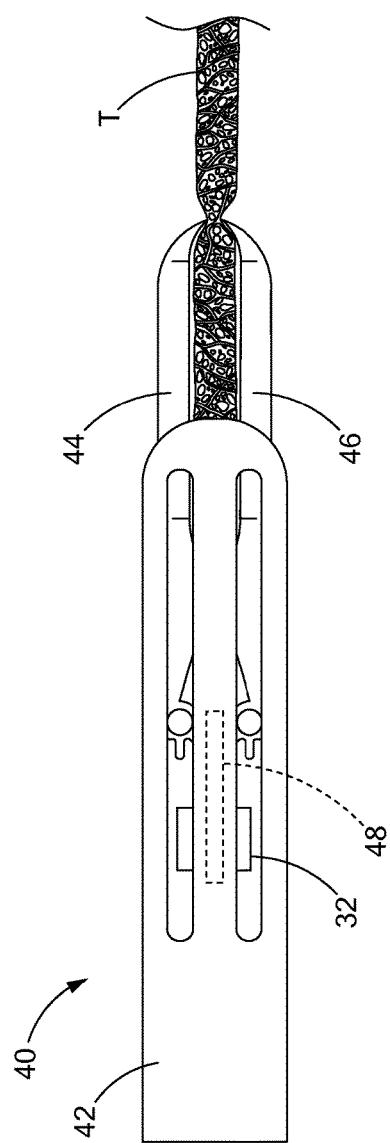

In the tissue receiving configuration shown in FIG. 10, the medical device 40 and its jaws 44, 46 may be positioned adjacent tissue T. As shown in FIG. 11, the tissue T may be placed between the first and second jaws 44, 46 and the jaws 44, 46 rotated back towards their position shown in FIG. 9. The tissue T has been shown as a single layer, although multiple layers may be clipped between the jaws 44, 46. Generally, proximal retraction of the drive wire 22 and the driver 48 again causes rotation of the first and second jaws 44, 46 to grasp the tissue T therebetween. As shown in FIG. 12, further proximal retraction of the drive wire 22 and driver 48 will cause the jaws 44, 46 to move longitudinally in a proximal direction (to the left on the page in FIG. 12).

Figure 13:
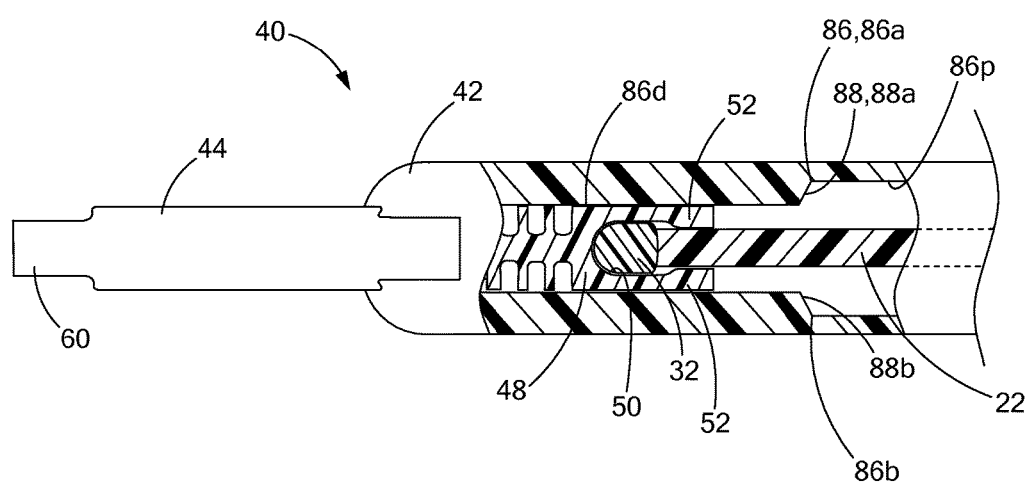
FIGS. 13 and 14 are top views, partially in cross-section, depicting operation of the medical system and device depicted in FIGS. 1-4.
Figure 14:
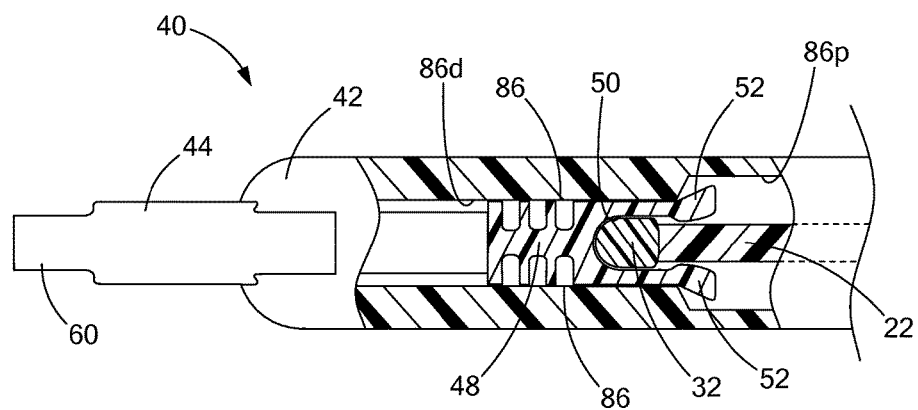

In order for the medical device 40 to serve as a clip and maintain its grasp on the tissue T, or to maintain the clipping of two layers of tissue against each other, the jaws 44, 46 may be locked in position and the drive wire 22 of the medical system 20 disconnected from the medical device 40. As shown in FIG. 13, the third guide surface 86 (which guides the driver 48) includes a proximal portion 86p and a distal portion 86d. The proximal portion 86p of the third guide surface 86 has a width (measured up and down on the page in FIG. 13) that is greater than a width of the distal portion 86d of the third guide 86. As previously discussed, the third guide surface 86 is formed by opposing surfaces or C-shaped channels 86a, 86b of the housing 42. The transition between the proximal portion 86p and distal portion 86d defines a shoulder 88, and namely two shoulders 88a, 88b on opposing sides of the housing 42. The shoulders 88a, 88b are sized and positioned to engage the locking tabs 52 located on the driver 48.

As shown in FIG. 13, when the driver 48 is located within the distal portion 86d of the third guide surface 86, the locking tabs 52 are forced radially inwardly into firm frictional engagement with the drive wire 22. Stated another way, the socket 50 formed by the driver 48 to receive the distal head 32 has an entrance which is narrowed by the inward deflection of the locking tabs 52. Preferably, the locking tabs 52 plastically deform rather than elastically deform, and the tabs 52 may be bent inwardly around the distal head 32 during initial assembly of the device, and thus sized for the distal portion 86d of the third guide surface 86. In this state depicted in FIG. 13, the drive wire 22 is firmly engaged with the driver 48 and hence the first and second jaws 44, 46.

When the drive wire 22 and driver 48 are retracted proximally, for example upon grasping tissue as shown in FIG. 12, the proximal end of the driver 48 is received within the proximal portion 86p of the third guide surface 86 which has a larger width that permits radially outward movement of the locking tabs 52. Accordingly, in the state depicted in FIG. 14, the locking tabs 52 may be loosely and detachably connected to the distal head 32 of the drive wire 22. That is, the proximal retraction of the jaws 44, 46 will be limited by either the tissue T engaging the distal end of the housing 42, or the pins 80 will abut the proximal ends of the slots 82a, 82b, 84a, 84b defining a first and second guide surfaces 82, 84. As such, when proximal movement of the jaws 44, 46 and the driver 48 are thus limited, further proximal movement of the drive wire 22 and its distal head 32 may be used to withdraw the distal head 32 from the socket 50 of the driver 48. This operation may also be used to further deflect the locking tabs 52 radially outwardly. An appropriate amount of distally directed force on the drive wire 22 causes the distal head 32 to move proximally through the locking tabs 52 and plastically deform them radially outwardly. In the event the natural elasticity of the tissue T tends to pull the jaws 44, 46 out from the housing towards their extended position, the locking tabs 52, 54 will abut the shoulders 88a, 88b of the third guide surface of the housing 42 to prevent further distal movement of the jaws 44, 46.

Figure 15:
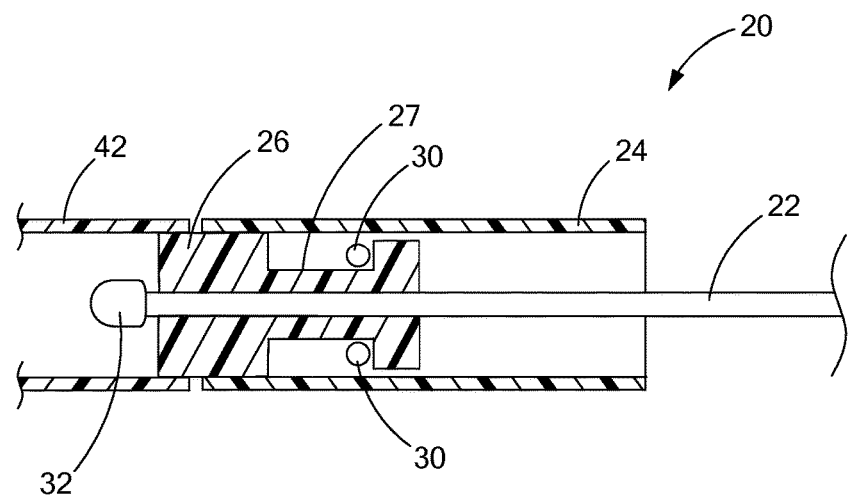
FIGS. 15 and 16 are cross-sectional views showing operation of the medical system and device depicted in FIGS. 1-4.
Figure 16:
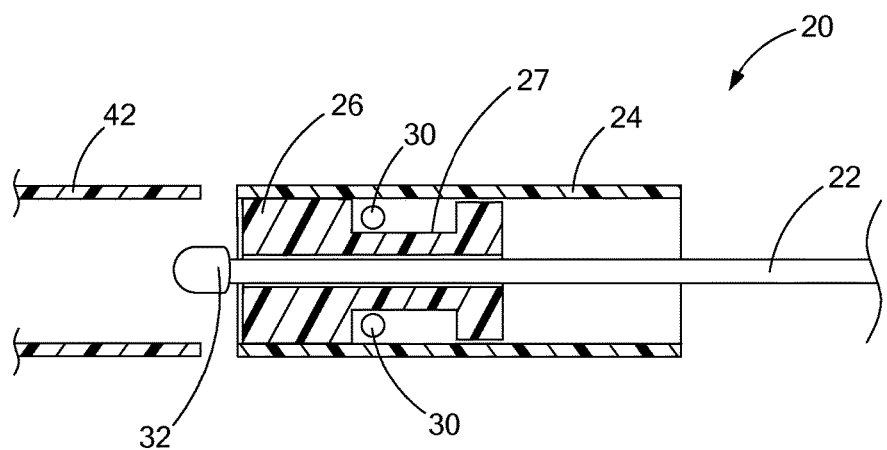

Turning now to FIGS. 15 and 16, upon still further proximal retraction of the drive wire 22 and distal head 32, the enlarged distal head 32 will abut the connection block 26 which is slidably fitted within the distal end 23 of the catheter 24. Sufficient proximal force on the drive wire 22 will overcome the frictional fit between the connection block 26 and the proximal end of the housing 42, thus moving the connection block 26 proximally (to the right on the page of FIGS. 15 and 16) to retract the connection block 26 within the tubular connector 24, as shown in FIG. 16. The catheter 24 can be used to provide a counterforce on the housing 42 while proximally retracting the drive wire 22 and connection block 26. Accordingly, the drive wire 22, catheter 24 and connection block 26 may be fully disconnected from the medical device 40, thereby leaving the first and second jaws 44, 46 and the housing 42 in a state having the tissue T clipped between the jaws 44, 46 and retained in vivo. The connection block 26 is retained at the distal end 24 of the catheter 24 via the pins 30, which are positioned within the recessed area 27 to engage the proximal and distal ends of the connection block 26 and limit its longitudinal movement.

The elongated catheter 24 (or other elongate tubular member such as a sheath, tube, scope or the like), which slidably encases the drive wire 22, extends proximally therealong to a proximal end of the system 20, and has a length suitable for placing the device 40 at any desired location within the body, while the proximal ends of drive wire 22 and catheter 24 are positioned outside of the body for use by the medical professional. Control handles (not shown) for controlling relative translation of the drive wire 22 and catheter 24 are well known in the art, and may be employed at the proximal end of the system 20.

Figure 17:
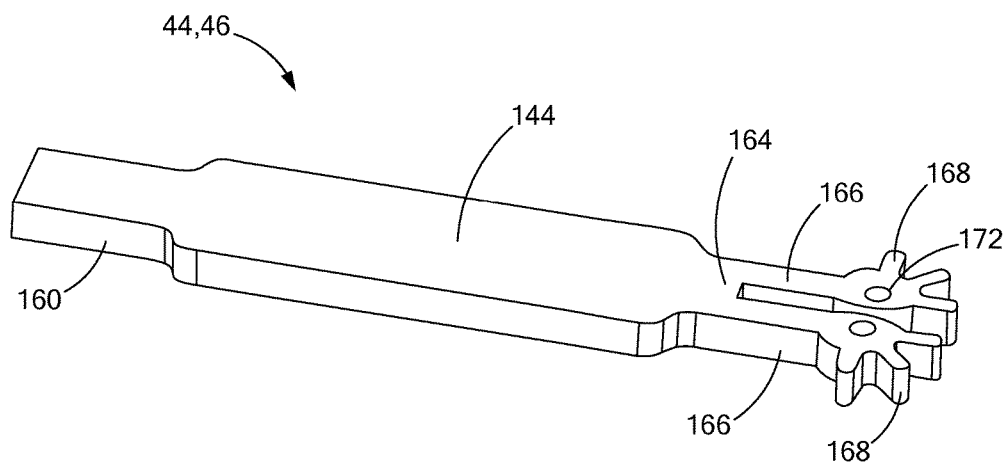
FIGS. 17 and 18 are a perspective view of an alternate embodiment of a grasping jaw forming a portion of the medical system and device of FIG. 1.
Figure 18:
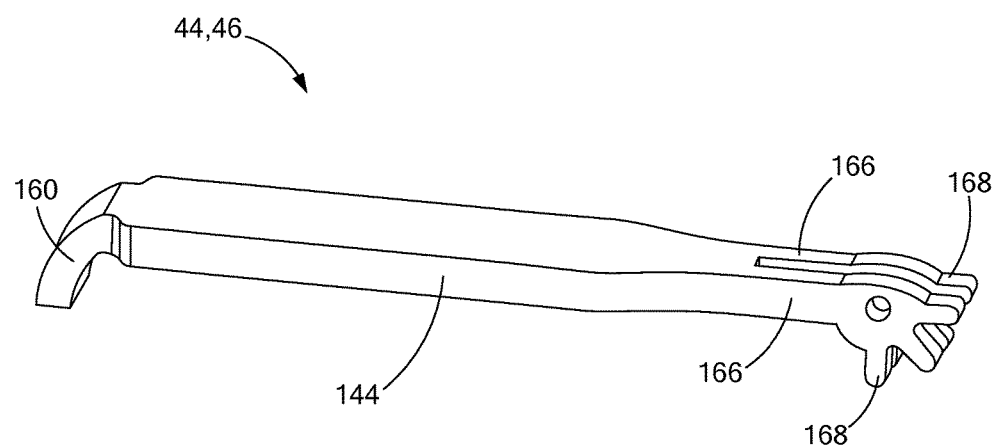

Another embodiment and method of forming the grasping jaws 44, 46 are shown in FIGS. 17-18. The jaws of the prior embodiment were generally machined, however the jaws 44, 46 may also be formed by stamping. A flat piece of metal preferably of medical grade stainless steel, is stamped into the shape 144 shown in FIG. 17. The shape includes a slightly narrow distal end 160 which then can be bent into the shape shown in FIG. 18 for grasping and engaging tissue. The distal end 160 may also be stamped to include a serrated edge, or other shapes or edge features depending upon the application. The proximal end 164 generally includes two arms 166 which lead to gears 168. As shown in FIG. 18, the gears 168 are grasped and then rotated about 90 degrees such that the gears 168 extend in a plane that is perpendicular to the plane of the sheet 144. The gears 168 also include a through-hole 172 for receiving a guiding pin. It will also be recognized that the jaws 44, 46 in this embodiment may also be formed of a single arm 166 and single gear 168.

Another embodiment of a driver 148 and drive wire 122 are shown in FIGS. 19-22. The driver 148 generally includes a socket 150 formed by two locking tabs 152. In this embodiment, a proximal portion of the locking tabs define slanted shoulders 154 which slope laterally outwardly for engagement with the third guide surface 86 in the housing 42 as previously discussed. The locking tabs 152 also include inner projections 153 which project laterally inwardly and separate the socket 150 into a distal portion 150d and a proximal portion 150p. The driver 148 again includes a central spine 156 and opposing teeth 158. In this embodiment, the distal end 166 of the driver 148 includes a pocket 168 defined by two inwardly projecting flanges 170, as will be discussed further herein. The two flanges 170 extend along a distal side of the pocket 168, and leave a gap therebetween for access to the pocket 168.

Figure 19:
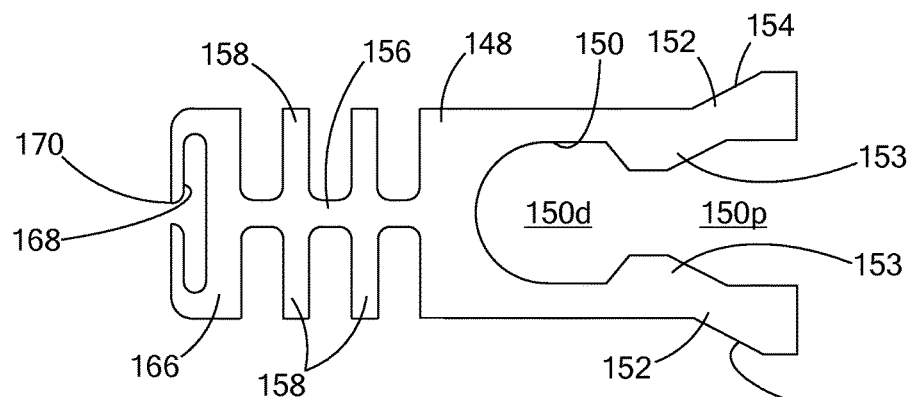
FIG. 19 is a plan view of an alternate embodiment of a driver forming a portion of the medical system and device of FIG. 1.
Figure 20:
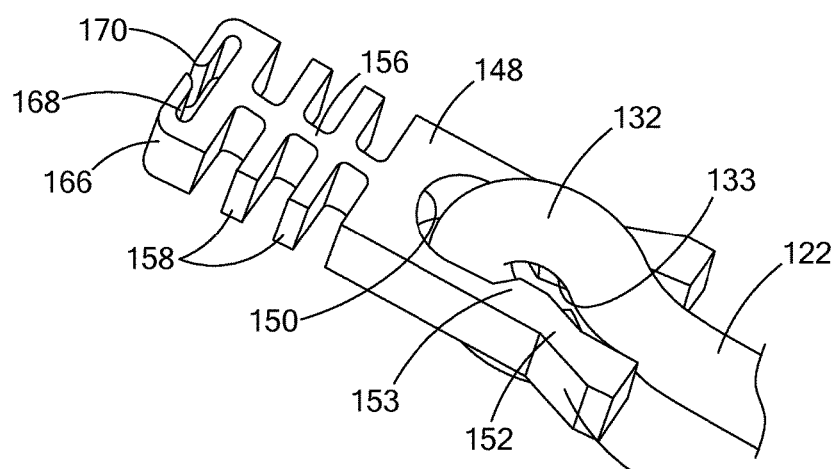
FIG. 20 is a perspective view of the driver of FIG. 19 shown attached to a drive wire.
Figure 21:
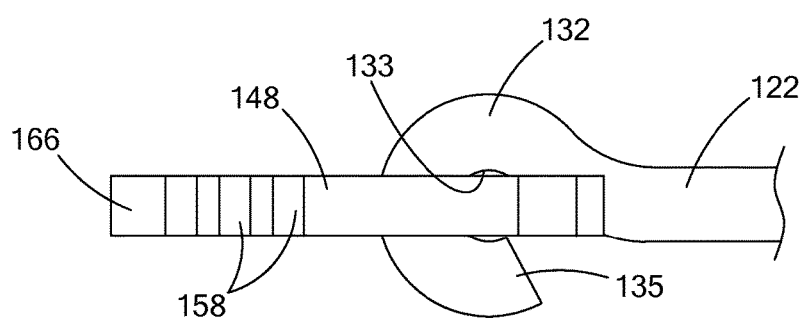
FIG. 21 is a side view of FIG. 20.

As seen in FIGS. 20 and 21, this embodiment of the drive wire 122 includes a distal head 132 which is formed by bending the distal end of the drive wire 122 into a semi-circular shape as shown, preferably spanning an arc of 180 degrees to 360 degrees. Accordingly, it can be seen that the distal head 132 defines an opening 133 that is sized to receive the inner projections 153 of the locking tabs 152. As shown, the distal portion 150d of the socket 150 receives the distal-most part of the curved distal head 132, while the proximal portion of the distal head 132 projects through the proximal portion 150p of the socket 150 and proximally away therefrom. As noted above, the locking tabs 152 here are structured to be plastically deformed, and thus after formation and connection to the drive wire 122 as shown in FIG. 19, the tabs 152 are bent radially inwardly to secure the projections 153 within the opening 133 of the socket 132. In this state, the exterior shoulders 154 of the locking tabs 152 are sized to fit within the third guide surface 86, and more particularly the distal portion 86d of the third guide surface 86 without further deformation.

Figure 22A:
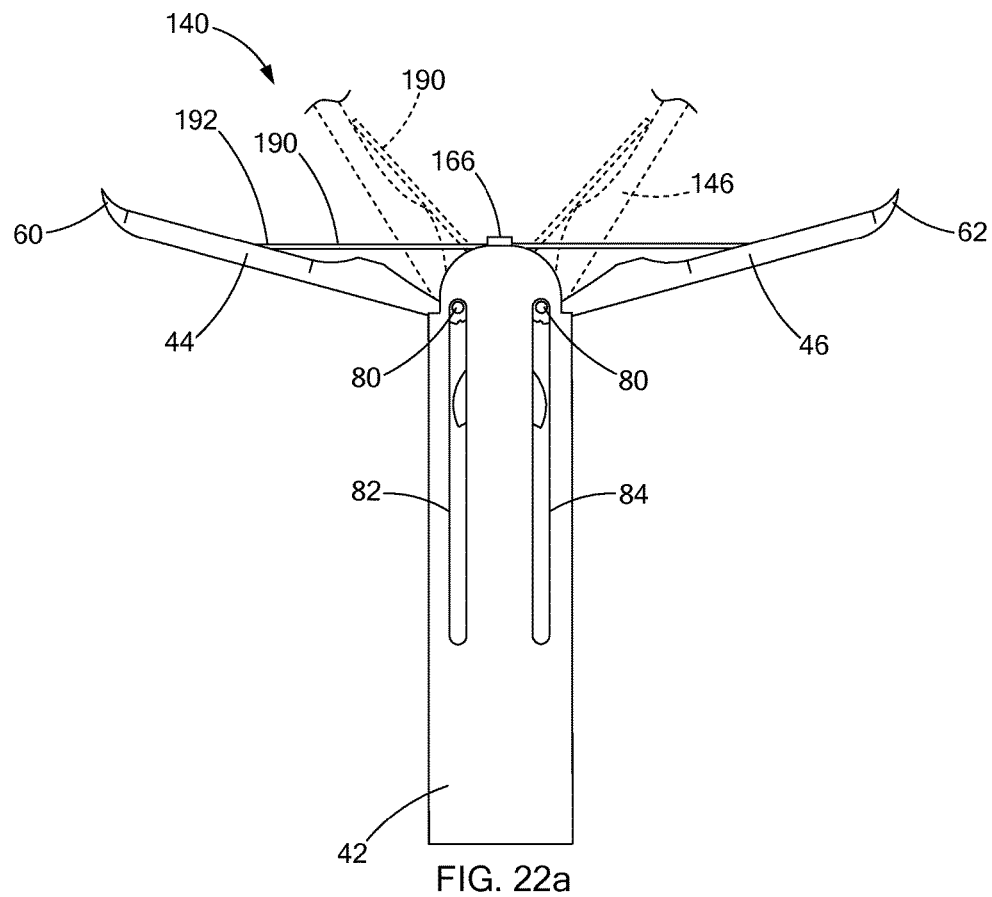
FIG. 22a is a plan view of an alternate embodiment of the medical device of FIG. 1.
Figure 22B:
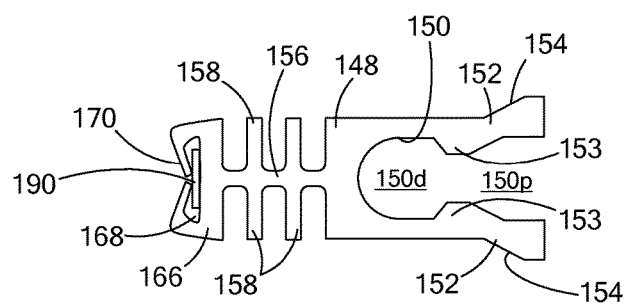

As shown in FIGS. 22a and 22b, another embodiment of the medical device 140 may include the housing 142, grasping arms 144, 146 just as in the prior embodiment, but in this embodiment include the alternate driver 148 and an additional biasing element, namely a biasing strip 190. As best seen in FIG. 22b, the distal end 166 of the driver 148 receives the biasing strip 190 within the pocket 168. The flanges 170 are bent inwardly and proximally as shown to firmly engage the metal strip 190 and fix it to the driver 148. The biasing strip 190 is preferably a thin strip formed from a sheet of resilient material, and more preferably a metal strip, e.g. formed of stainless steel, nitinol or other super elastic alloy that is biocompatible. Accordingly, it will be recognized that as the driver 148 is moved proximally to cause the jaws 144, 146 to close, the biasing strip 190 will be forced into a V-shape or U-shape, as shown by the dotted lines in FIG. 22a. That is, the biasing strip 190 has a straight shape in its natural, unbiased, configuration, and when bent into the V-shape it exerts a radially outward force on the jaws 144, 146. This biasing force provides the jaws 144, 146 with smooth rotation and transition between the open and closed positions. It will also be recognized that the biasing strip 190 could also have its original, unbiased position formed as a V-shape or a U-shape, and be affixed to the jaws 144, 146 such that it exerts a radially inward biasing force. The free ends 192 of the metal strip 190 simply press against the jaws 44, 46, but are not fixed or rigidly attached thereto.

Figure 23:
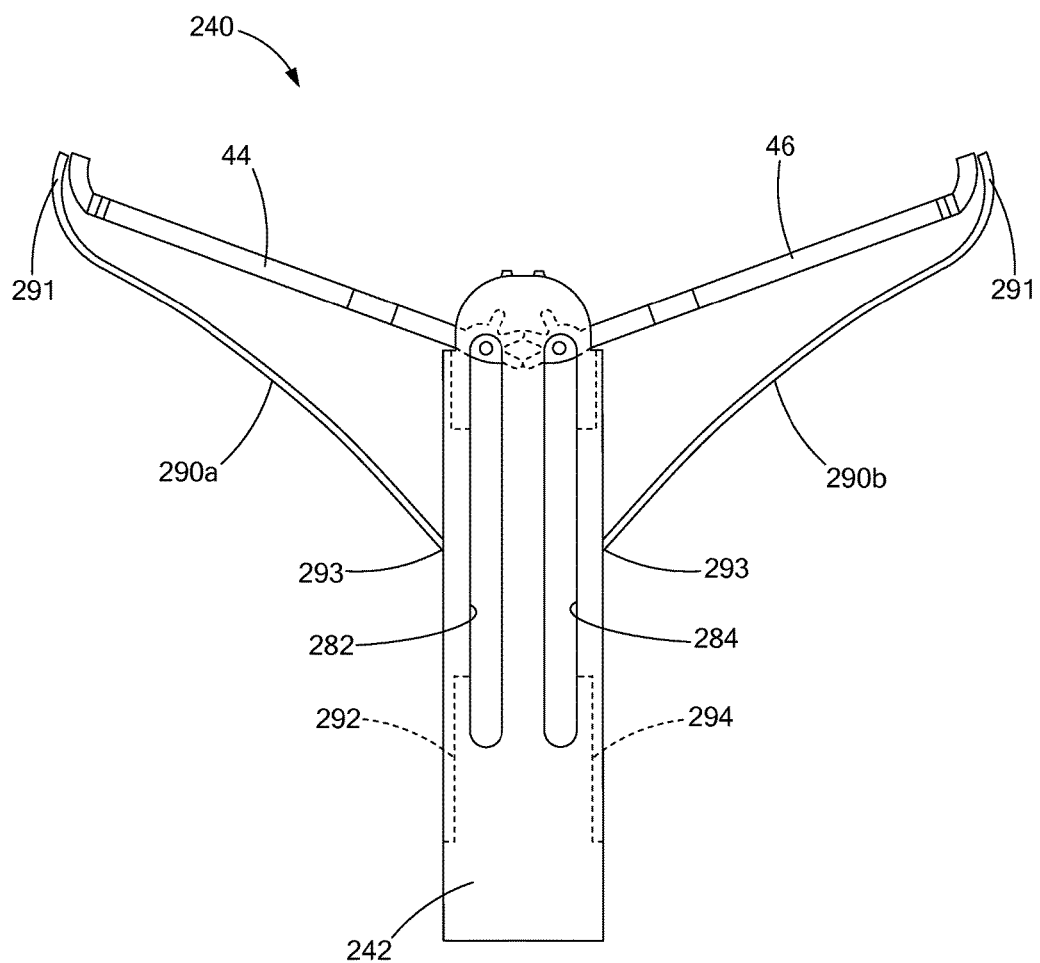
FIG. 23 is a plan view of another alternate embodiment of the medical device depicted in FIG. 1.
Figures 24, 25:
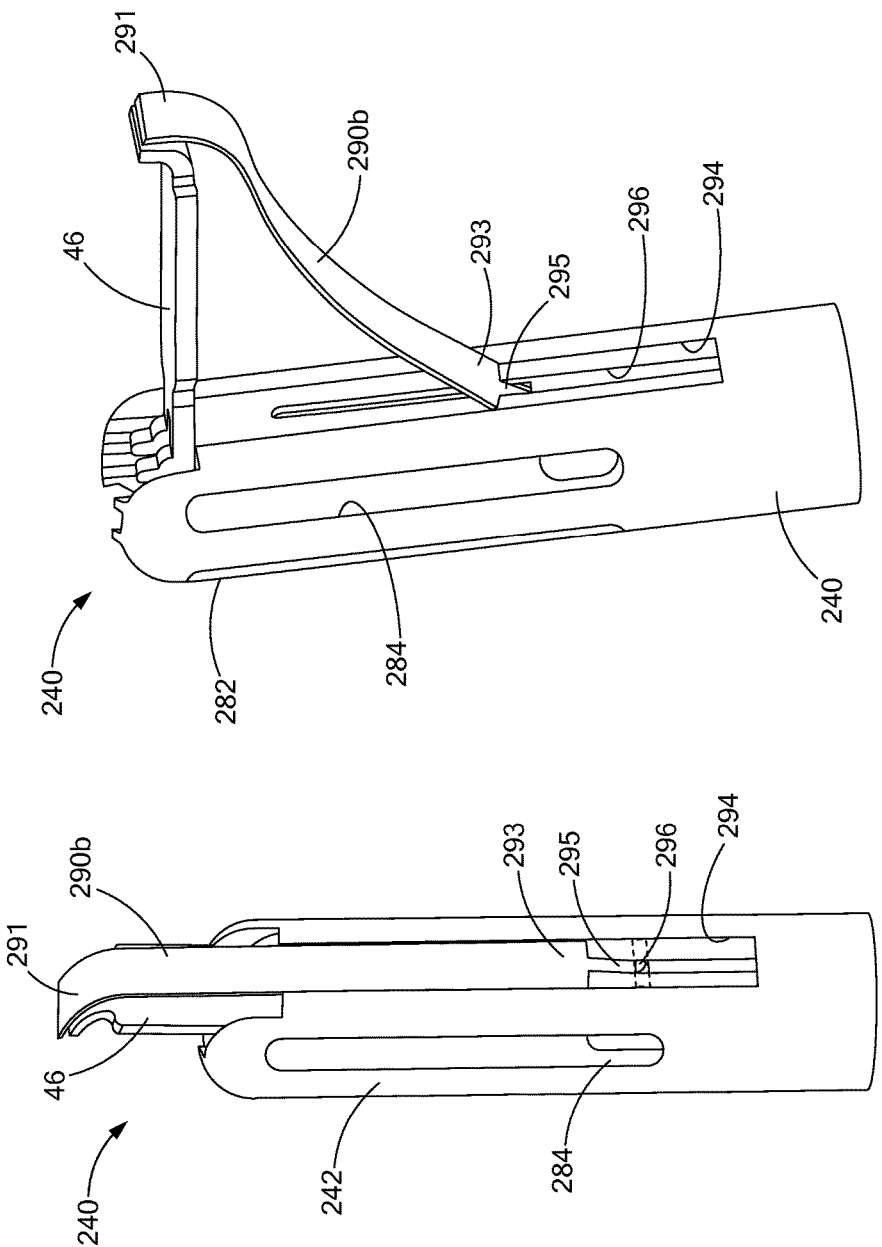
FIGS. 24 and 25 are a perspective views showing operation of the medical device depicted in FIG. 23.

Turning to FIG. 23, another embodiment of the medical device 240 is shown, again including a housing 242 and opposing jaws 244, 246 that are slidably attached thereto. The housing 242 again includes first and second guides 282, 284 for guiding movement of the jaws 244, 246. In this embodiment however, each jaw 244, 246 includes a biasing strip 290a, 290b, respectively. The distal ends 291 of the strips 290a, 290b are fixedly attached to the exterior of the jaws 244, 246, preferably at their distal ends, and preferably by way of an adhesive, soldering, welding, or other known bonding techniques. As best seen in FIGS. 24 and 25, the housing 240 includes two exterior channels 294 on opposite sides of the housing 240 (one being shown in FIGS. 24 and 25) which are sized to receive the resilient strips 290a, 290b such that they are flush with the exterior surface of the housing in the closed/retracted configuration. The proximal ends 293 of the strips 290a, 290b include a T-shaped formed by a base 295 and cross bar 296. The base 295 extends through a smaller slot 296 formed through the housing 240. The slots 296 are coextensive with the channels 294. The cross bar 296 rides along the interior of the housing 240 and maintains the slidable connection between the strips 290 and the housing 240. Accordingly, it can be seen that the proximal ends 293 of the strips 290a, 290b are slidably and pivotably attached to the housing 240 via the channel 294 and its slot 296, allowing the strips 290a, 290b to travel with the grasping jaws 44, 46 as shown between their open and closed positions as shown in FIGS. 24 an 25.

Figure 26:
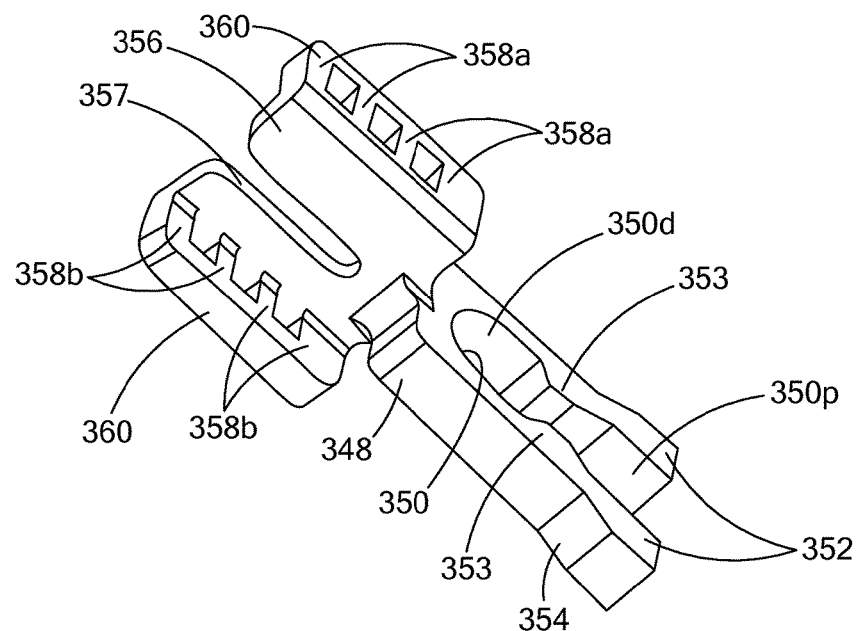
FIGS. 26 and 27 are perspective and end views, respectively, of another embodiment of a driver forming a portion of the medical system and device depicted in FIG. 1.
Figure 27:
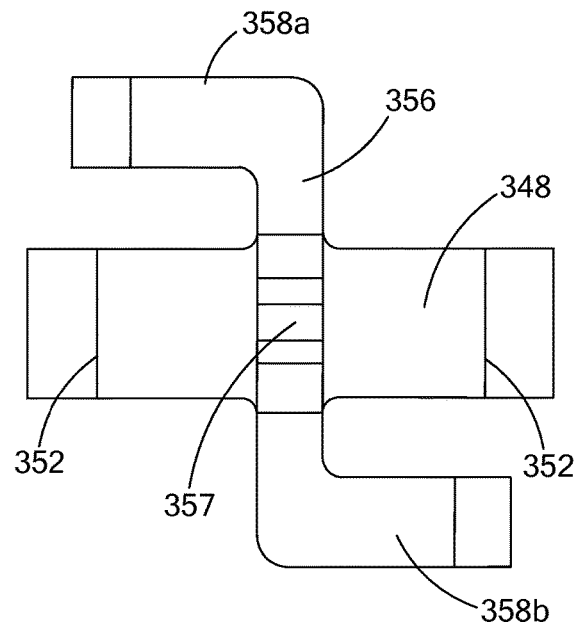
Figure 28:
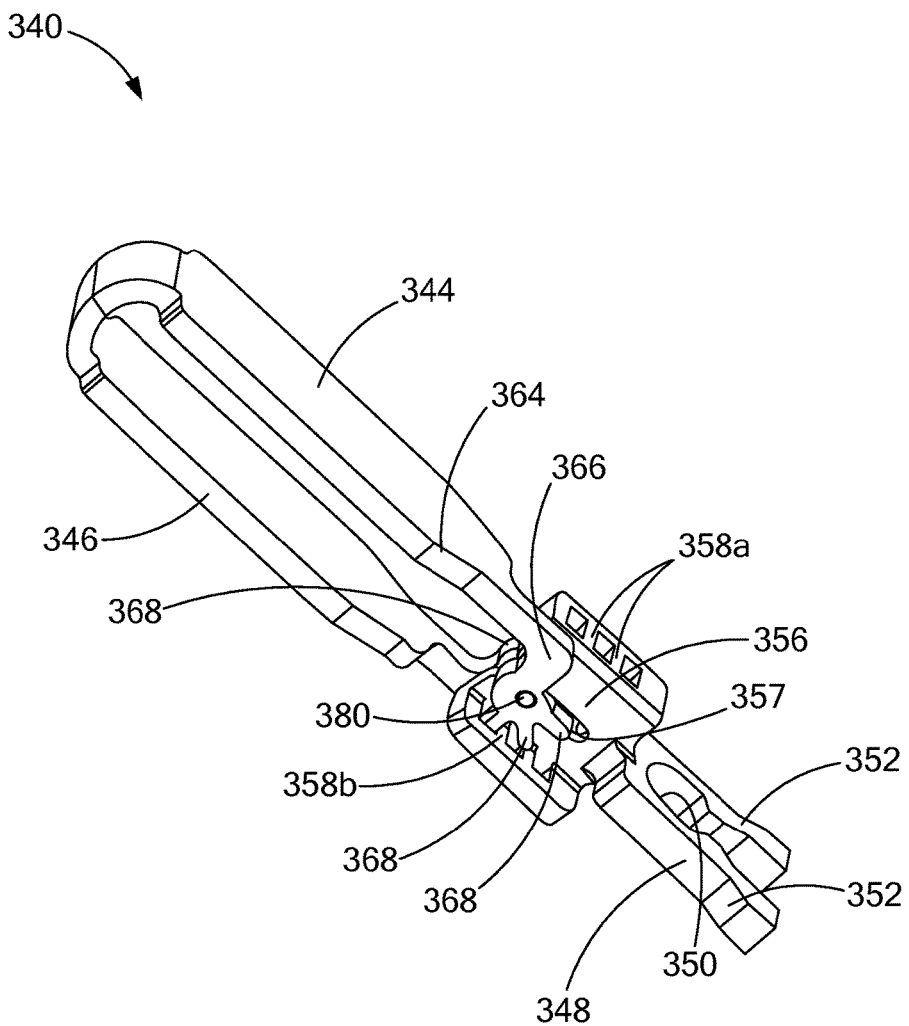
FIG. 28 is a perspective view of the driver of FIGS. 25-26 shown attached to the jaws.
Figure 29:
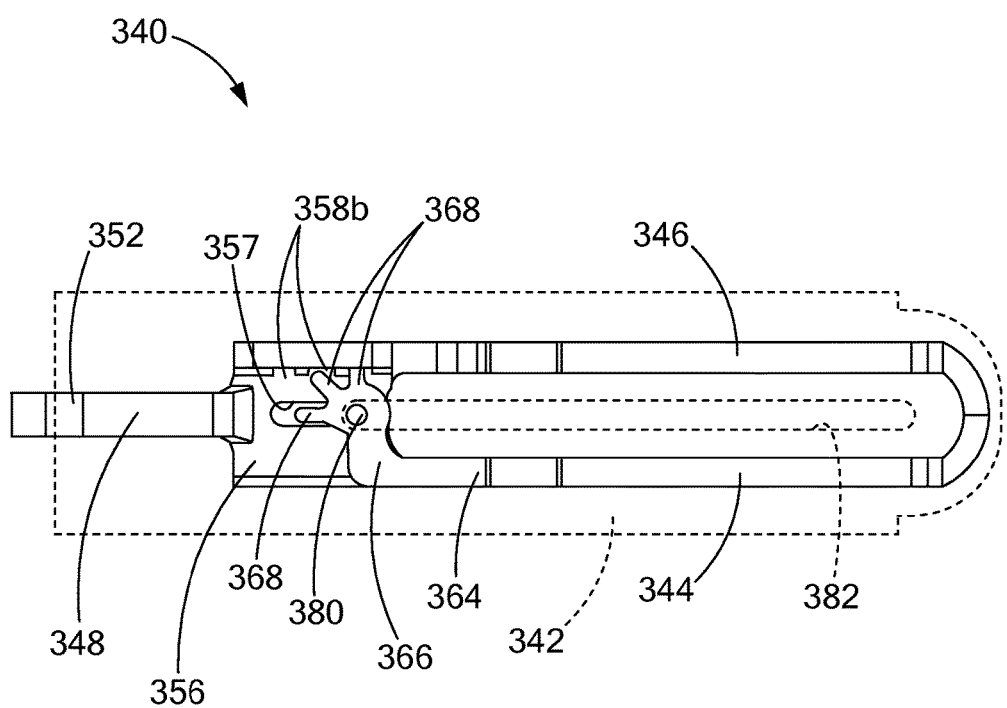
FIGS. 29 and 30 are plan views showing operation of the driver and jaws depicted in FIG. 28.
Figure 30:
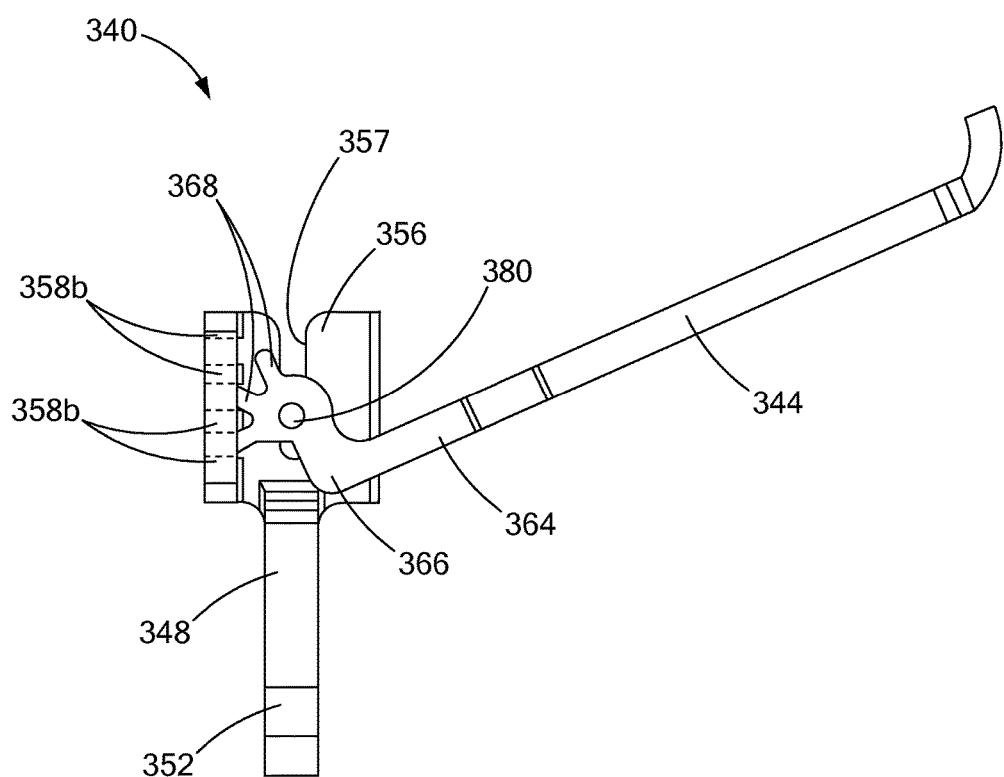

Turning now to FIGS. 26-30, another embodiment of a driver 348 is shown. As best seen in FIGS. 26 and 27, the driver 348 again includes a socket 350 formed by two locking tabs 352 which have inner projections 353 and outer shoulders 354, and which divide the socket 350 into a distal portion 353 and a proximal portion 350p. Unlike the prior embodiments of the driver, in this embodiment the distal portion defines a geared rack that has a Z-shape. Generally, a central plate 356 replaces the central spine 56, 156 of the prior embodiments, and the plate 356 extends in a plane that is parallel to the longitudinal plane of the housing 342 (FIG. 29). The plane of the central plate 356 is also perpendicular to a plane of the proximal half of the driver 348 (i.e. that which includes the socket 350 and tabs 352). A first set of teeth 358a project laterally away from the central plate 356 in a first direction, while a second set of teeth 358b project laterally away from the central plate 356 in a second direction. The first and second sets of teach 358a, 358b extend from opposite ends of the central plate 356, and the first and second directions are generally opposite each other. The sets of teeth 358a, 358b are each securely held to the central plate 356 by two outer frames 360 which extend around the periphery of the teeth 358a, 358b.

Accordingly, and as best seen in FIG. 28, the medical device 340 includes first and second grasping jaws 344, 346 each having a proximal end 366 and gear teeth 368 which have been bent to project orthogonally away from a main body of the jaw 344. Accordingly, the first set of teeth 358a receive the gear 368 of the second jaw 346, while the second set of teeth 358b receive the gear 368 of the first jaw 344. Notably, having the proximal ends 366 of the jaws 344, 346 bent laterally/orthogonally as shown allows a single pin 380 to be passed through the gears 368 and thus shared by both jaws 344, 346. Still further, and as shown in FIG. 29, the housing 342 may thus include only a single guide surface 382 formed by a single slot on each lateral side of the housing 342 for receiving the ends of the single pin 380. It can be seen that the first and second jaws 344, 346 thereby share a single guide surface 382 (a jaw guide surface) and guide slot, thus ensuring their coordinated operation and smooth opening and closing.

As also shown in FIG. 29, a slot 357 is formed in the central plate 356, and is aligned with the pin 380 and jaw guide surface 382 to receive the pin 380 as the driver 348 moves forwardly relative to the jaws 344, 346. As discussed above and shown in FIG. 30, when the pin 380 (shared by proximal ends 366 and gears 368 of the jaws 344, 346) has hit the distal end of the single jaw guide surface 382, the driver 348 will continue moving distally to cause the gears 368 to rotate via the rack/teeth 358a, 358b of the driver 348, thereby inducing rotation of the jaws 344, 346.

Figure 31:
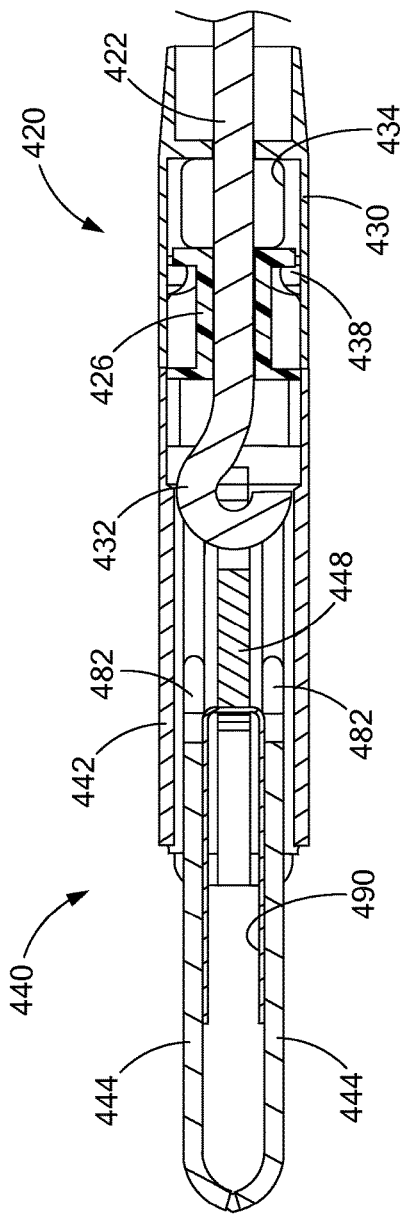
FIGS. 31 and 32 are cross-sectional views of another embodiment of the medical system and device depicted in FIG. 1.
Figure 32:
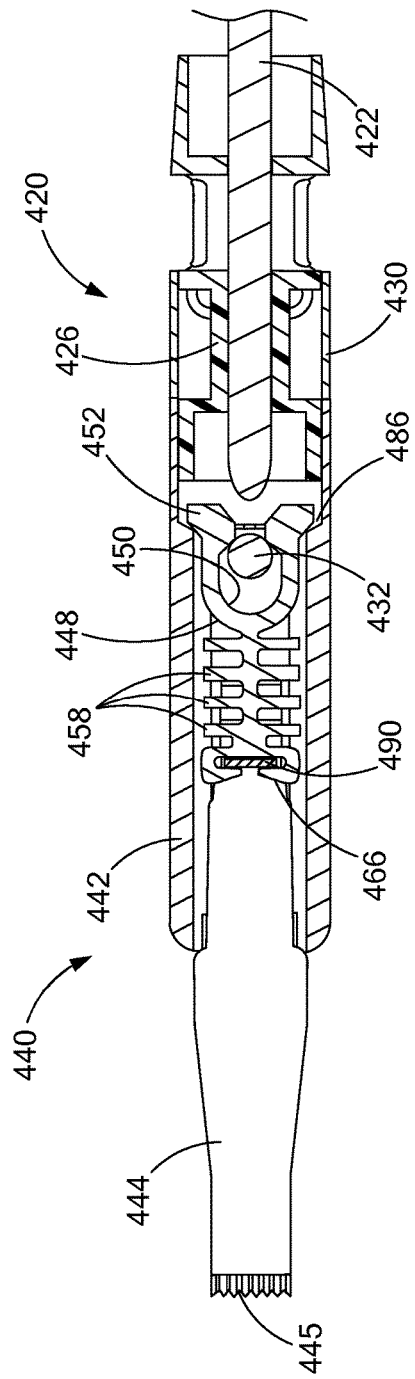
Figure 33:
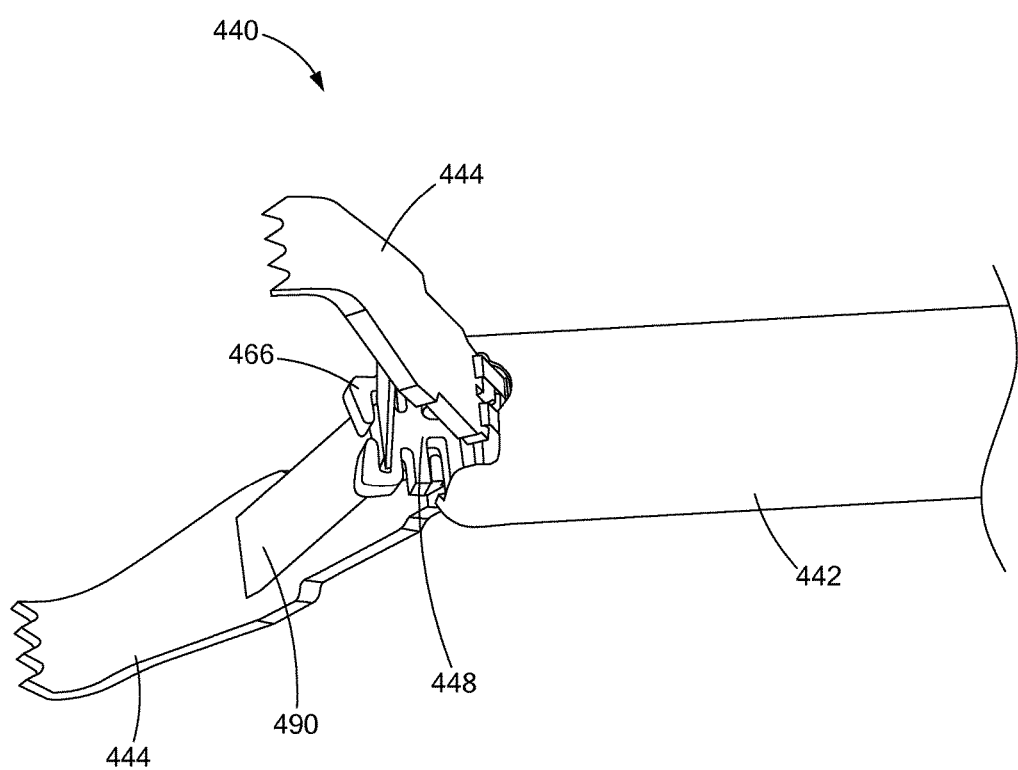
FIG. 33 is a perspective view of the medical system and device depicted in FIGS. 31 and 32.

Turning to FIGS. 31-33, another embodiment of the medical system 420 and medical device 440 are depicted. In this embodiment, medical system 420 again includes a drive wire 422 having a distal head 432 which is formed by bending the distal end of the drive wire 422 into the shape shown. The medical system 420 also includes a catheter attachment 430 which is generally a tubular member that is connected to the distal end of the catheter 24 and is used to slidably receive the connection block 426. The catheter attachment 430 includes a pair of openings 434 to provide access to the control wire 422 and the connection block 426, whereby a tool may be used to hold the connection block 426 in either a retracted or extended position, as further described in U.S. Appl. No. 61/391,878 filed concurrently herewith, and Appl. No. 61/391,875 filed concurrently herewith, the disclosures of which are hereby incorporated by reference in their entirety.

The medical device 440 includes a housing 442 which is detachably connected to the catheter 24 and its catheter attachment 430 via the connection block 426. The housing 442 slidably receives the pair of jaws 444 which are connected to the drive wire 422 via the driver 448. As with the previous embodiments, the driver 448 includes a socket 450 defined by locking tabs 452 which releasably engage the distal head 432 of the drive wire 422. The distal portion of the driver 448 includes a plurality of teeth 458 which define a gear or rack which serves to drive rotation of the jaws 444 as previously described. The distal end 466 of the driver 448 includes a pocket defined by flanges which are used to fixedly engage the biasing strip 490. The housing 442 further defines a pair of guiding surfaces or slots 482 which guide the longitudinal and rotational movement of the jaws 444.

In this embodiment, the jaws 444 and housing 442 are structured such that in the fully retracted position (shown), the jaws 44 project (at least partially) out distally from the end of the housing 442. As best seen in FIG. 32, as the distal head 432 is pushed through the locking tabs 452 they are plastically deformed outwardly to engage the shoulders 446 in the housing, and the jaws 444 are fully retracted. In this way, the length of the housing 442 can be shortened, as can the guiding slots 482 therein for guiding the jaws 444. It can also be seen in FIG. 32 that the distal ends of the jaws 444 include serrations 445 or other structures which may aid in gripping tissue.

It is also noted that in this embodiment, as with all prior embodiments, the drive wire 422 is capable of transmitting rotational force and torque (e.g. from the proximal operating end of the system 20/420) through the distal head 432 and the driver 448 to the jaws 444. As such the medical device 440 may be rotated via rotation of the drive wire 422, i.e. the jaws 444, jaw pins (e.g. 80), housing 442, and driver 448 all rotate as a unit relative to the catheter 24. Inasmuch as the housing 442 may also be non-rotatably connected to the connection block 426 (e.g. depending on the friction therebetween), the connection block 426 may also rotate within the catheter attachment 430 (or the catheter, e.g. 24) when the catheter attachment 430 is not used. Accordingly, the orientation of the jaws 444 may be rotated through rotation of the proximal end of the drive wire 422 to orient the jaws relative to the tissue or material being grasped or clipped. It has been found that forming the drive wire 422 out of a solid nitinol wire has provided good torque transmission for rotation of the medical device 440.

It has also been found that having the jaws 444 project at least partially out of the housing 442 in their fully retracted position allows the orientation of the jaws 444 to be visualized so that it is easier to rotate the jaws 444 prior to opening and closing them around tissue. Still further, additional tissue may be encapsulated in the jaws 444 before the tissue abuts the distal end of the housing 442. The distance which the jaws 444 project from the housing 442 may be varied depending upon a particular application, i.e. sized to correspond to the thickness of the tissue or the type of procedure being formed to insure good spacing between the distal ends of the jaws 444 and the distal end of the housing 442.

Figure 34:
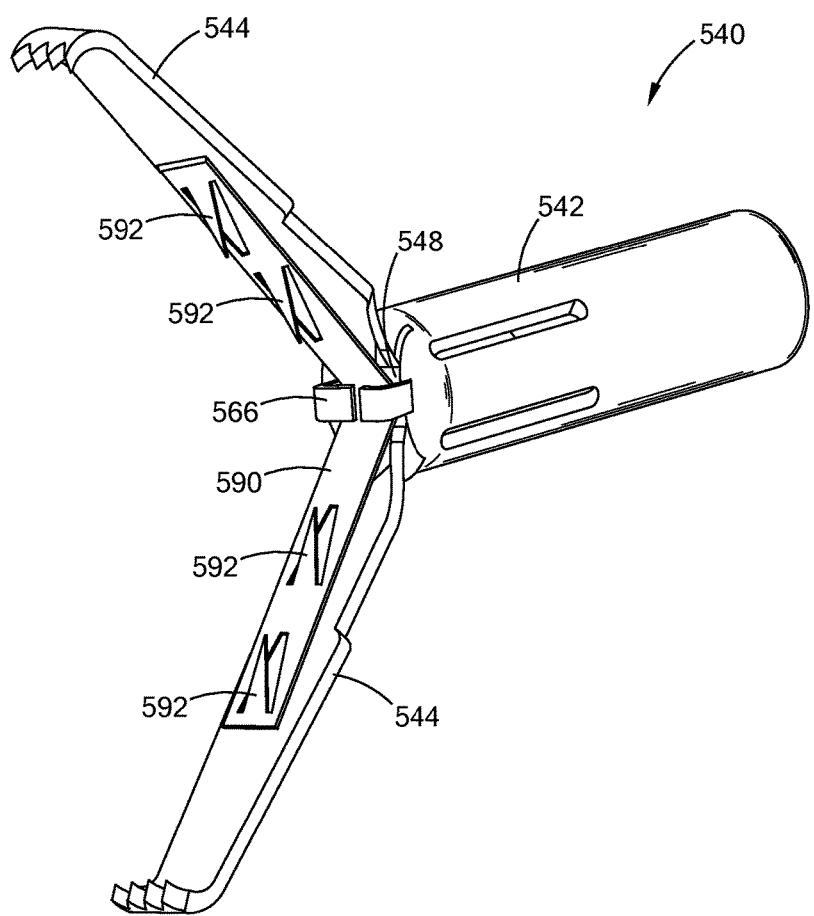
FIG. 34 is a plan view of another alternate embodiment of the medical device depicted in FIG. 1.
Figure 35:
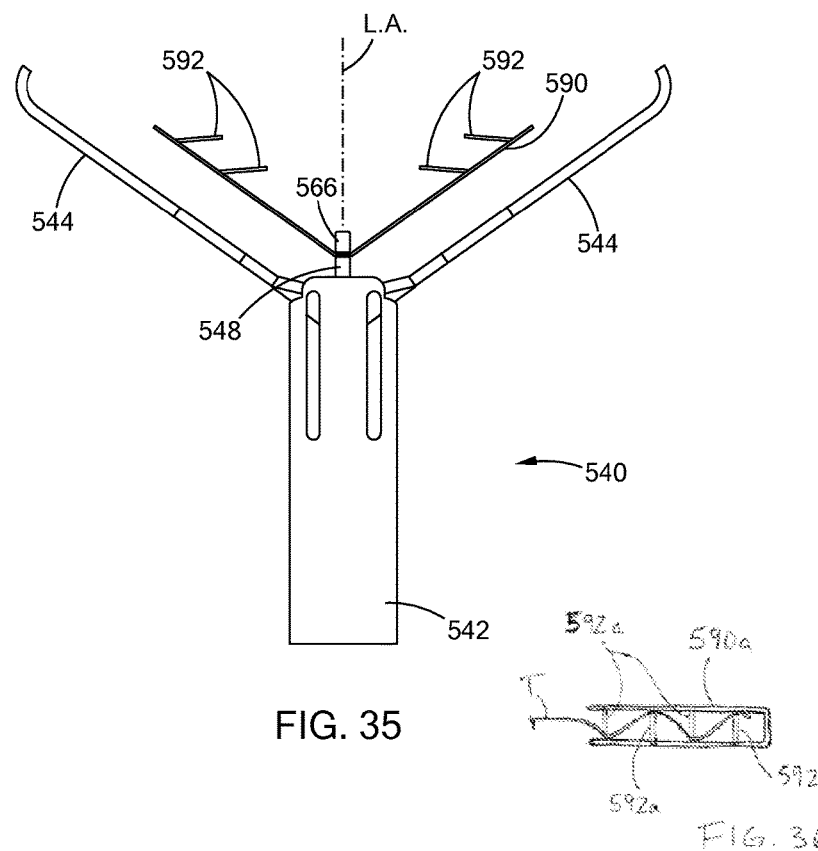
FIGS. 35 and 36 are side views showing operation of the medical device of FIG. 34.
Figure 36:
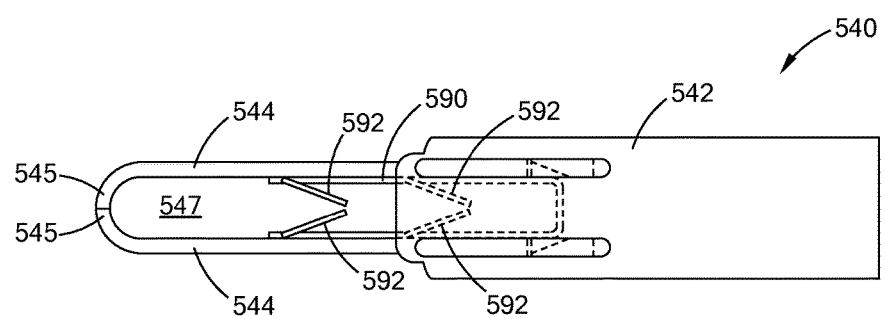

Turning to FIGS. 34-36, another embodiment of the medical device 540 is depicted. In this embodiment, the medical device 540 again includes the remainder of the medical system from any of the previous embodiments, as well as the housing 542 and pair of jaws 544 as in the previous embodiments. All prior embodiments of the medical systems and devices, or features thereof, may be used with this medical device 540. In this embodiment, the driver 548 again includes a distal end 566 defining a pocket and flanges that are used to fixably engage a biasing strip 590. The biasing strip 590 is biased radially outward, and engages the jaws 544 through most, if not all, of their outward rotation. In this embodiment, the biasing strip 590 is stamped to provide at least one, and preferably a plurality of, prongs 592; four prongs 592 being shown in the depicted embodiment. The prongs 592 are preferably formed directly from the strip 590 by stamping, cutting or other material processing, although the prongs 592 could be separately formed and attached to the strip 590. The prongs preferably have a free end which is sharp to facilitate engagement of the tissue via the medial device 540.

In the open configuration of the medical device 540, shown in FIG. 35, the prongs 592 extend radially inwardly and are generally orthogonal to the longitudinal axis L. A. In the closed configuration of the medical device 540, shown in FIG. 36, the prongs 592 project radially inwardly and proximally, preferably at an angle of 15° to 90° (relative to an axis of the respective strip portion), and more preferably about 15° to 45°. As best seen in FIG. 36, the prongs 592 are preferably arranged in opposing pairs such that two prongs 592 project towards each other to define a small lateral space therebetween. Alternatively, the free ends of the prongs 592 may touch the free end of the respective opposing prong 592. Still further, in another variation shown in FIG. 36a, the strip 590a may have prongs 592a on the opposing strip portions that are alternating (longitudinally spaced apart in the closed configuration), and have a length such that the free ends of the prongs 592a touch a flat portion of the opposing strip portion in the closed configuration, and provide a zig-zag shaped tortuous path for the tissue T. Any combination of the above-described prong variations may be employed together.

Inasmuch as the jaws 544 have distal ends 545 forming a talon shape, the jaws 544 define a gripping space 547 therebetween. While the distal ends 545 of the jaws 544 directly engage each other, tissue that is thinner than the lateral distance between the jaws 544 (i.e. a lateral width of the gripping space 547) is only partially restrained. Accordingly, the prongs 592 extend into the gripping space 547 to effectively reduce the lateral distance between the jaws 544 in the area of the gripping space 547 and directly engage the tissue positioned between the jaws 544. The biasing strip 590 and its prongs 592 may be incorporated into any of the prior embodiments of the medical system and device.

Figure 39:
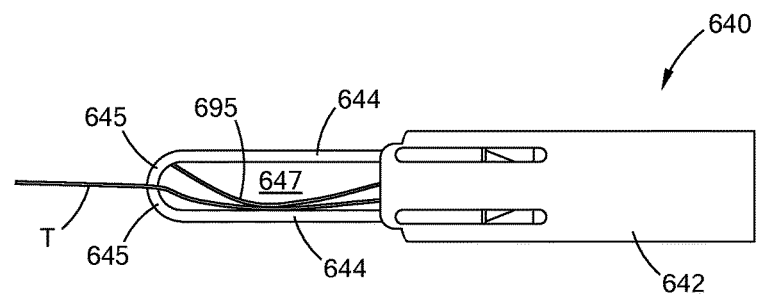

Turning now to FIGS. 37-39, another embodiment of the medical device 640 is depicted. All prior embodiments of the medical systems and devices, or features thereof, may be used with this medical device 640. In this embodiment, the medical device again includes a housing 642 that slidably and rotationally receives the pair of jaws 644 which are driven through the motion by a driver 648. To facilitate engagement of the tissue between the jaws 644, a gripping strip 695 is provided on one of the jaws 644, which may be referred to herein as the first jaw. The gripping strip 695 is a thin flat strip, preferably formed of a biocompatible metal or plastic such as stainless steel or nitinol, and has a width equal to or less than a width of the jaws 644.

The gripping strip 695 has a distal portion 697 and a proximal portion 698. The distal portion 697 preferably includes a distal end directly and/or fixedly attached to the distal end of the first jaw 644, such as by a weld 696. Although a weld 696 has been shown, the distal portion 697 of the gripping strip 695 may be attached to the distal end 645 of the first jaw 644 the other know means such as adhesives, various welding or soldering techniques, or other mechanical connectors or fasteners. As previously discussed, the jaws 644 include distal ends 645 having a curved talon shape and preferably the weld 696 is formed at a proximal portion of the curved distal end 645 or immediately adjacent the curved distal end 645 of the first jaw 644. In short, a distal end of the gripping strip 695 is attached to a distal portion of the jaw 644.

The proximal portion 698 of the gripping strip 695 includes a proximal end which is free floating, but preferably is sized and structured to loosely engage a proximal end of the first jaw 644. As best seen in FIGS. 37 and 38, the gripping strip 695 is bent into a concave shape (facing the first jaws 644) such that the distal portion 697 projects radially inwardly toward the longitudinal axis, and preferably beyond the axis and towards the opposing jaws 644 (in the closed configuration), while the proximal portion 698 of the gripping strip 695 projects back radially towards the first jaw 644 (i.e. the jaw to which it is attached). The proximal portion 698 and proximal end of the gripping strip 695 are positioned radially outside of the driver 648 and longitudinal axis. The proximal end of the gripping strip 695 may be attached to the first jaw 644 if desired.

As best seen in FIG. 38, in a closed configuration of the medical device 640, the distal portion 697 of the gripping strip 695 projects all the way across the gripping space 647 defined between the jaws 644 and engages the opposing (or second) jaw 644. The proximal portion 698 of the gripping strip 695 then projects back towards the first jaw 644 as best seen in FIG. 39. In the closed configuration of the medical device 640, when tissue T is positioned between the jaws 644 and within the gripping space 647, the gripping strip 695 serves to press the tissue T firmly against the opposing jaw 644 while the distal end 645 of the jaws 644 firmly engage the tissue T therebetween. In this way, the medical device 640 is provided with an improved grip on the tissue T.

Figure 40:
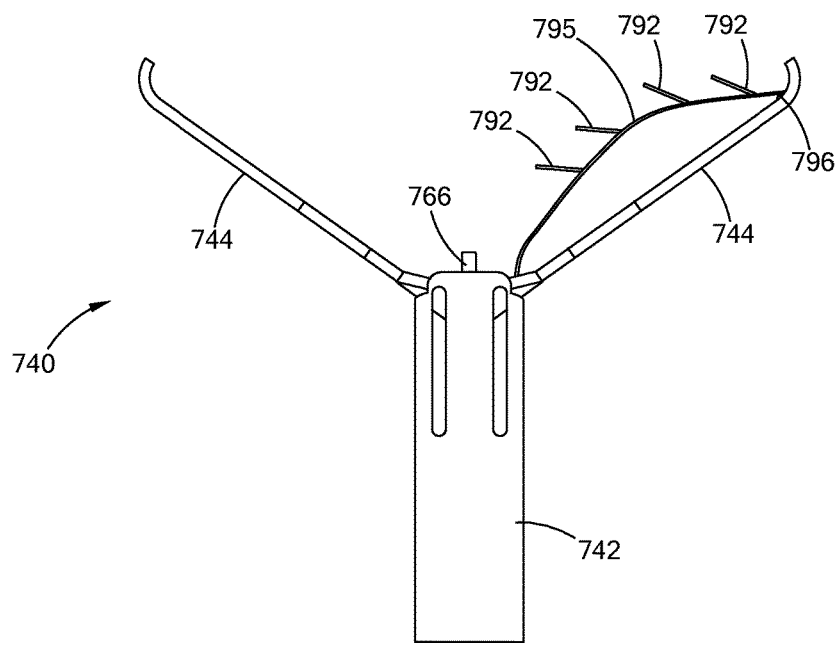
FIG. 40 is a side view of another alternate embodiment of the medical device depicted in FIG. 1.

Turning now to FIG. 40, yet another embodiment of the medical device 740 is illustrated. All prior embodiments of the medical systems and devices, or features thereof, may be used with this medical device 740. This embodiment is substantially identical to the embodiment of FIGS. 37-39, and includes a housing 742 slidably and rotatably receiving a pair of jaws 744 which are driven by a driver 766. A gripping strip 795 having a shape similar to the gripping strip 695 described above, is attached at its distal end to a distal portion of a first jaw 744 via a weld 796. In this embodiment, the gripping strip 795 is provided with a plurality of prongs 792, four prongs being shown in FIG. 40. A prong 792 are similar to the prongs 592 shown and described in the embodiment of FIGS. 34-36, and may have similar shapes and be formed similarly thereto. Briefly, the prong 792 preferably are stamped directly from the gripping strip 795 and have a triangular shape that has a terminal end which is sharp to engage, preferably by slightly piercing, the tissue between the jaws 744.

Figure 42:
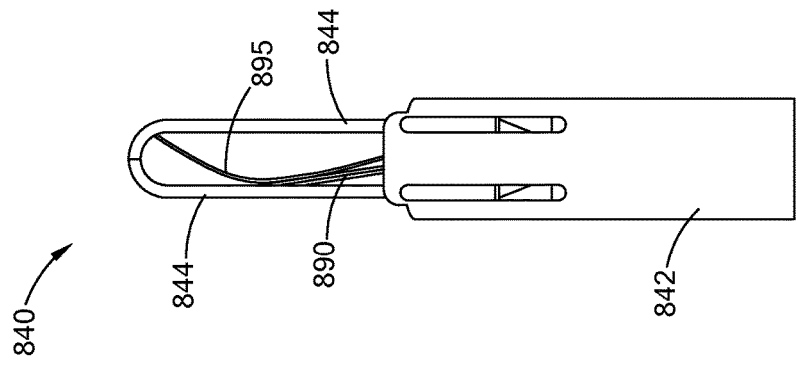
FIGS. 41 and 42 are side views showing operation of another alternate embodiment of the medical device depicted in FIG. 1.
Figure 41:
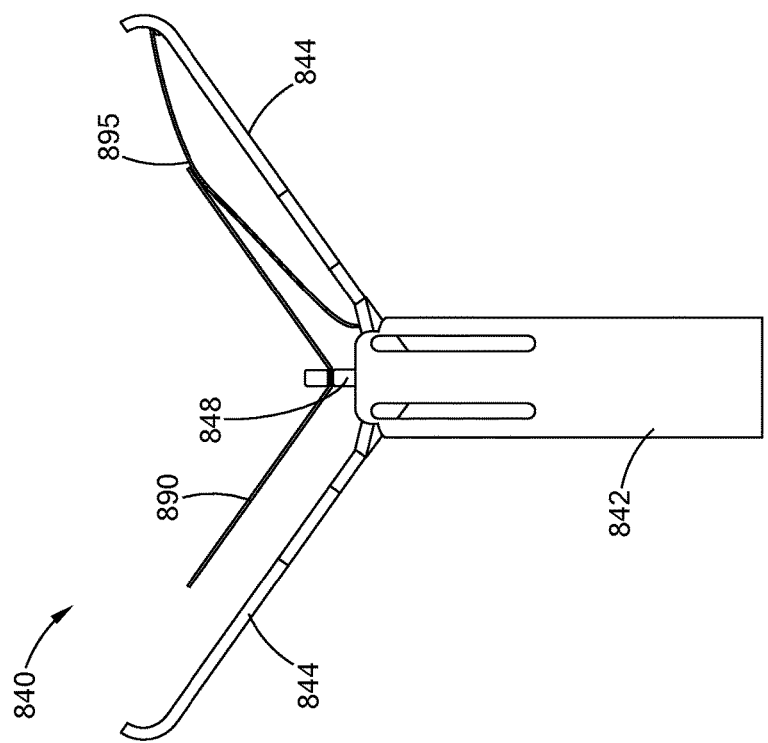

Turning now to FIGS. 41 and 42, another embodiment of the medical 850 is shown and described. In this embodiment, all the prior embodiments of the medical system and devices, or features thereof, may be used with the medical device 840. In particular, this embodiment shows how a gripping strip 895 may be employed in conjunction with a biasing strip 890. The biasing strip 890 is substantially identical to any of the biasing strips previously described such as strips 190, 490, and is fixedly attached to a distal end of the driver 848. Likewise, the gripping strip 895 is substantially identical to the gripping strips 695, 795 described in FIGS. 37-40, and includes a distal end attached to a distal end portion of the first jaw 844. The portion of the gripping strip 895 that overlaps with the biasing strip 890 is positioned radially outside the biasing strip 890. Accordingly, the biasing strip 890 directly engages the gripping strip 895, which in turn is fixedly attached to the first jaw 844 to transfer the radially outward biasing force from the biasing strip 890 to the first jaw 844 (having the gripping strip 895). In the closed configuration of the medical device 840, shown in FIG. 42, the gripping strip 895 preferably has a rigidity greater than the biasing strip 890 such that it continues to extend towards and engage the opposing jaw 844 before curving laterally away from the opposing jaw, thereby pressing both the tissue and the biasing strip 890 against the opposing jaw 844.

While the gripping strip 895 has been shown positioned radially outside the biasing strip 890 in the embodiment of FIGS. 41-42, since the proximal end of the gripping strip 895 is free floating, it can also be positioned radially inside a corresponding portion of the biasing strip. For example, as shown in the embodiment of the medical system 940a in FIG. 43, the medical device 940a includes a housing 942 slidably and rotationally receiving opposing jaws 944a. Here the gripping strip 995a is substantially identical to the previously described gripping strips, at the proximal portion and proximal end thereof is positioned radially inside the biasing strip 990a as shown in FIG. 43. Preferably, the proximal end of the gripping strip 995a is located at the juncture of the biasing strip 990a and the driver 948a. Again here the driver 948a includes a distal end 966a fixedly attached to the biasing strip 990a. Likewise, in this embodiment a second gripping strip 995a has been shown attached to the opposing jaw 944a and similarly constructed and attached to the jaw 944a as in the prior embodiments. Accordingly, the biasing strip 990a may directly engage and outwardly bias the jaws 944a, while the gripping strips 995a are attached to the distal ends of the jaws 944a but are sized and structured to substantially fill the gripping space between the jaws 944a.

A similar variation to add a second gripping strip is shown in another embodiment of the medical device 940b and FIG. 44. As with the embodiment of 943, the medical device 940b includes a housing 942b slidably and rotationally receiving a pair of opposing jaws 944b driven by a driver 948b. Again here the driver 948a includes a distal end 966b fixedly attached to the biasing strip 990b. In this embodiment, two gripping strips 995b are again provided, however the gripping strips 995b are positioned radially outside the biasing strip 990b. Accordingly, the biasing strip 990b presses against the opposing gripping strips 995b, which are directly attached to the opposing jaw 944*b*, to thereby bias the jaws radially outwardly. At the same time, the gripping strips 995*b* substantially fill the gripping space between the jaws 944*b* to firmly engage the tissue over a greater length of the jaws 944*b*. All prior embodiments of the medical systems and devices, or features thereof, may be used with the medical devices 940*a* and 940*b*.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for engaging tissue, the medical device comprising:
   a housing defining an internal passageway and a longitudinal axis extending between proximal and distal ends of the housing;
   a first jaw rotatable relative to the housing, the first jaw having proximal and distal ends;
   a second jaw rotatable relative to the housing, the second jaw having proximal and distal ends, the first and second jaws including portions proximal to their distal ends that are spaced apart to define a gripping space therebetween;
   a driver engaged with the proximal ends of the first and second jaws, longitudinal movement of the driver rotating the first and second jaws relative to the housing; and
   a gripping strip positioned between the first and second jaws, the gripping strip fixedly attached to a distal portion of the first jaw, the gripping strip projecting towards the second jaw and positioned to engage tissue between the second jaw and the gripping strip, the gripping strip projecting through the gripping space to define a space between the first jaw and the gripping strip, wherein the gripping strip has a concave shape with a concavity facing the first jaw.

2. The medical device of claim 1, wherein, in a closed position of the medical device, the distal ends of the first and second jaws engage each other, and the gripping strip projects through the gripping space to a location immediately adjacent the second jaw.

3. The medical device of claim 2, wherein the gripping strip engages the second jaw in the closed position when no tissue is located between the first and second jaws.

4. The medical device of claim 1, wherein the gripping strip includes a distal portion extending radially towards the second jaw, and a proximal portion extending radially away from the second jaw.

5. The medical device of claim 1, wherein the gripping strip includes a proximal end that is not attached to the first jaw such that the proximal end of the gripping strip is free floating for movement relative to the first jaw.

6. The medical device of claim 1, wherein the gripping strip includes at least one projection extending radially inwardly towards the longitudinal axis, the at least one projection sized and structured to engage the tissue between the first and second jaws.

7. The medical device of claim 6, wherein the at least one projection has a triangular shape terminating in a sharp distal end for piercing tissue.

8. The medical device of claim 6, wherein the at least one projection is formed by stamping the gripping strip.

9. The medical device of claim 1, further comprising a biasing strip positioned between the first and second jaws, the biasing strip operatively connected to at least one of the first and second jaws to bias the jaws radially.

10. The medical device of claim 9, wherein the proximal end of the gripping strip is positioned between the biasing strip and the first jaw.

11. The medical device of claim 9, wherein the proximal end of the gripping strip is positioned between the biasing strip and the second jaw.

12. The medical device of claim 9, wherein the biasing strip is fixed to a distal end of the driver and moves therewith.

13. The medical device of claim 1, further comprising a second gripping strip positioned between the first and second jaws, the second gripping strip attached to a distal portion of the second jaw, the second gripping strip projecting towards the first jaw and positioned to engage tissue between the first and second gripping strips.

14. The medical device of claim 1, wherein the gripping strip is separately formed from, and attached to, the first jaw.

15. The medical device of claim 1, wherein the gripping strip is laterally positioned to be aligned with the longitudinal axis.

16. The medical device of claim 1, wherein the gripping strip, from the distal end to the proximal end, extends towards and then away from the second jaw.

17. The medical device of claim 1, wherein the first and second jaws are non-detachably connected to the housing.

18. A medical device for engaging tissue, the medical device comprising:
    a housing defining an internal passageway and a longitudinal axis extending between proximal and distal ends of the housing;
    a first jaw rotatable relative to the housing, the first jaw having proximal and distal ends;
    a second jaw rotatable relative to the housing, the second jaw having proximal and distal ends;
    a driver engaged with the proximal ends of the first and second jaws, longitudinal movement of the driver rotating the first and second jaws relative to the housing; and
    a gripping strip positioned between the first and second jaws, the gripping strip attached to a distal portion of the first jaw, the gripping strip projecting towards the second jaw and positioned to engage tissue between the second jaw and the gripping strip, wherein the gripping strip includes a distal end fixedly attached to the first jaw and a proximal end that is not fixedly attached to the first jaw, wherein the gripping strip, from the distal end to the proximal end, extends towards and then away from the second jaw.

19. The medical device of claim 18, wherein the gripping strip is separately formed from, and attached to, the first jaw.

20. The medical device of claim 18, wherein the gripping strip engages the second jaw in the closed position when no tissue is located between the first and second jaws.

21. The medical device of claim 18, wherein the proximal end of the gripping strip is free floating for movement relative to the first jaw.

22. The medical device of claim 18, wherein the gripping strip has a concave shape with a concavity facing the first jaw.

23. The medical device of claim 18, further comprising a biasing strip positioned between the first and second jaws, the biasing strip operatively connected to at least one of the first and second jaws to bias the jaws radially.

24. The medical device of claim 23, wherein the proximal end of the gripping strip is positioned between the biasing strip and one of the first and second jaws.

25. The medical device of claim 18, wherein, in a closed position of the medical device, the distal ends of the first and second jaws engage each other, and the gripping strip projects through the gripping space to a location immediately adjacent the second jaw.

26. The medical device of claim 25, wherein the gripping strip engages the second jaw in the closed position when no tissue is located between the first and second jaws.

\* \* \* \* \*